(12) United States Patent
Cohen-Vered et al.

(10) Patent No.: US 7,294,687 B2
(45) Date of Patent: Nov. 13, 2007

(54) PARENTERAL FORMULATIONS OF A PEPTIDE FOR THE TREATMENT OF SYSTEMIC LUPUS ERYTHEMATOSUS

(75) Inventors: Sharon Cohen-Vered, Kfar Sava (IL); Esmira Naftali, Rosh HaAyin (IL); Vera Weinstein, Mevaseret Zion (IL); Adrian Gilbert, Ra'anana (IL); Ety Klinger, Tel Aviv (IL)

(73) Assignee: TEVA Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 10/758,572

(22) Filed: Jan. 14, 2004

(65) Prior Publication Data

US 2004/0180059 A1    Sep. 16, 2004

Related U.S. Application Data

(60) Provisional application No. 60/439,950, filed on Jan. 14, 2003.

(51) Int. Cl.
*A61K 38/00*    (2006.01)
*A61K 31/74*    (2006.01)
(52) U.S. Cl. .................... 530/300; 424/78.08
(58) Field of Classification Search .............. 514/12; 424/185.1; 530/300
See application file for complete search history.

(56) References Cited

U.S. PATENT DOCUMENTS

| | | | |
|---|---|---|---|
| 4,656,158 A | 4/1987 | Matsuo et al. | |
| 5,126,249 A | 6/1992 | Becker et al. | |
| 5,134,127 A | 7/1992 | Stella et al. | |
| 5,376,645 A | 12/1994 | Stella et al. | |
| 5,646,131 A | 7/1997 | Badwan et al. | |
| 5,997,856 A * | 12/1999 | Hora et al. | 424/85.2 |
| 6,228,363 B1 | 5/2001 | Naparstek | |
| 6,407,079 B1 * | 6/2002 | Muller et al. | 514/58 |
| 6,613,536 B1 | 9/2003 | Mozes et al. | |
| 2002/0054872 A1 | 5/2002 | Napastek | |
| 2004/0127408 A1* | 7/2004 | Mozes | 514/12 |
| 2005/0008634 A1* | 1/2005 | Cohen-Vered et al. | 424/131.1 |

FOREIGN PATENT DOCUMENTS

| | | |
|---|---|---|
| EP | 0495049 | 7/1992 |
| WO | WO9630057 | 10/1996 |
| WO | WO9931066 | 6/1999 |
| WO | WO03067848 | 9/2002 |

OTHER PUBLICATIONS

Anderson, B.D. and Flora, K.P. "The Practice of Medicinal Chemistry" (Chapter 34, pp. 739-754, edited by Camille Georges Wermuth, Academic Press 1996.*
U.S. Appl. No. 10/758,397, filed Jan. 14, 2004, Sharon Cohen-Vered et al.
Audibert et al. (1981) Active antitoxic immunization by a diphtheria toxin synthetic oligopeptide. *Nature*, 289:593-4.
Axelrod, O. and Mozes, E. (1986) Analysis of the biological functions and fine specificity of (T,G)-A-L specific T cell clones. *Immunobiology*, 172:99-109.
Bombardier C. et al. (1992) Derivation of the SLEDAI. A disease activity index for lupus patients. The Committee on Prognosis Studies in SLE. *Arthritis Rheum.*, 35:630-40.
Conlon, P.J. (1983) A rapid biologic assay for the detection of interleukin I. *J. Immunol.*, 134:1280-2.
Dayan M. et al. (2000) Immune response of SLE patients to peptides based on the complementarity determining regions of a pathogenic anti-DNA monoclonal antibody. *J. Clin. Immunol.*, 20(3):187-94.
Dean G.S. et al. (2000) Cytokines and systemic lupus erythematosus. *Ann. Rheum. Dis.*, 59:243-51.
Eilat, E., et al. (2000) Prevention of systemic lupus erythematosus-like disease in (NZB×NZW)F1 mice by treating with CDR1- and CDR3- based peptides of pathogenic autoantibody. *J. Clin. Immunol.*, 20:268-78.
Eilat, E., et al. (2001) The mechanism by which a peptide based on complementarity determining region-1 of pathogenic anti-DNA antibody ameliorates experimental SLE. *Proc. Natl. Acad. Sci. U.S.A.*, 98: 1148-53.
Fricke, H. et al. (1991) Idiotype specific T-cell lines inducing experimental systemic lupus erythematosus in mice. *Immunology*, 73:421-7.
Fricke, H. et al. (1990) Induction of experimental systemic lupus erythematosus in mice by immunization with a monoclonal anti-La autoantibody. *Int. Immunol.*, 2:225-30.
Gearing, A.J.H. et al. (1994) Processing of tumor necrosis factor-alpha precursor by metalloproteinases. *Nature*, 370:555-7.
Gijbels, K. et al. (1992) Gelatinase in the cerebrospinal fluid of patients with multiple sclerosis and other inflammatory neurological disorders. *J. Neuroimmunol.*, 41:29-34.
Goetzl, E.J. et al. (1996) Matrix metalloproteinases in immunity. *J. Immunol.*, 156:1-4.
Guedez, L. et al. (1996) The role of metalloproteinases and their inhibitors in hematological disorders. *Crit. Rev. Oncog.*, 7:205-25.
Hay, E.M. et al. (1993) The BILAG index: a reliable and valid instrument for measuring clinical disease activity in systemic lupus erythematosus. *O. J. Med.*, 86:447-58.

(Continued)

*Primary Examiner*—Robert Mondesi
*Assistant Examiner*—Anand Desai
(74) *Attorney, Agent, or Firm*—John P. White; Cooper & Dunham LLP

(57) ABSTRACT

The subject invention provides a pharmaceutical composition comprising an aqueous carrier; from 0.1 mg/ml to 20 mg/ml of the composition of a pharmaceutically acceptable salt of a peptide having the structural formula $NH_2$-Gly Tyr Tyr Trp Ser Trp Ile Arg Gln Pro Pro Gly Lys Gly Glu Glu Trp Ile Gly-$COOH$;

and a substituted β-cyclodextrin in an amount effective to dissolve the peptide in the aqueous carrier, wherein the composition has a pH between 4 and 9, a process for preparation, and a method of alleviating symptoms of systemic lupus erythematosus (SLE) in a human subject comprising administering to the human subject the pharmaceutical composition.

25 Claims, 6 Drawing Sheets

OTHER PUBLICATIONS

Isenberg, D.A., et al. (1984) Anti-DNA antibody idiotypes in systemic lupus erythematosus. *Lancet*, 2(8400):417-22.

Isenberg, D.A., et al. (1985) Detection of cross-reactive anti-DNA antibody idiotypes on renal tissue-bound immunoglobulins from lupus patients. *J. Clin. Invest.*, 76(1):287-94.

Katchalski, E. et al. (1955) Molecular weight distribution of linear and multichain polyamino acids. Statistical analysis. *J. Am. Chem. Soc.*, 77:6175-82.

Kotajima, L., et al., (1998) Increased levels of matrix metalloproteinase-3 in sera from patients with active lupus nephritis. *Clin. Exp. Rheumatol.*, 16(4):409-15.

Mendlovic, S. et al. (1988) Induction of a systemic lupus erythematosus-like disease in mice by a common human anti-DNA idiotype. *Proc. Natl. Acad. Sci. U.S.A.*, 85:2260-4.

Mendlovic, S. et al. (1989) The role of anti-idiotypic antibodies in the induction of experimental systemic lupus erythematosus in mice. *Eur. J. Immunol.*, 19:729-34.

Mendlovic, S. et al. (1990) The genetic regulation of the induction of experimental SLE. *Immunology*, 69:228-36.

Mozes, E. et al. (1989) Direct binding of a myasthenia gravis related epitope to MHC class II molecules on living murine antigen-presenting cells. *EMBO J.*, 8:4049-52.

Muller, G.M. et al. (1982) Anti-influenza response achieved by immunization with a synthetic conjugate. *Proc. Natl. Acad. Sci. U.S.A.*, 79:569-73.

Nakamara, T. et al. (1993) Gene expression of metalloproteinases and their inhibitor in renal tissue of New Zealand black/white F1 mice. *Clin. Sci.*, 85:295-301.

Paemen, L. et al. (1994) Evaluation of gelatinases and IL-6 in the cerebrospinal fluid of patients with optic neuritis, multiple sclerosis and other inflammatory neurological diseases. *Eur. J. Neurol.*, 1:55-63.

Ruiz, P.J. et al. (1994) Induction of experimental systemic lupus erythematosus in mice by immunization with the f(ab)2 fragment of the human anti-DNA monoclonal antibody carrying the 16/6 idiotype. *Immunol. Lett.*, 41:79-84.

Saren, P. et al. (1996) TNF-alpha and IL-1 beta selectively induce expression of 92-kDa gelatinase by human macrophages. *J. Immunol.*, 157:4159-65.

Schnolzer, M. et al. (1992) In situ neutralization in Boc-chemistry solid phase synthesis. Rapid, high yield assembly of difficult sequences. *Int. J. Pept. Protein Res.*, 40: 180-93.

Segal, R. et al. (1997) Kinetics of cytokine production in experimental systemic lupus erythematosus: involvement of T helper cell 1/T helper cell 2-type cytokines in disease. *J. Immunol.*, 158:3009-16.

Shoenfeld, Y. et al. (1983) Idiotypic cross-reactions of monoclonal human lupus autoantibodies. *J. Exp. Med.*, 158:718-30.

Shoenfeld, Y. et al. (1982) Production of autoantibodies by human-human hybridomas. *J. Clin. Invest.*, 70:205-8.

Sthoeger, Z.M. et al. (1993) Monoclonal anticardiolipin antibodies derived from mice with experimental lupus erythematosus: characterization and the induction of a secondary antiphospholipid syndrome. *J. Clin. Immunol.*, 13:127-38.

Tan, E.M. et al. (1982) The 1982 revised criteria for the classification of systemic lupus erythematosus. *Arthritis Rheum.*, 25:1271-7.

Theofilopoulos, A.N. et al. (1999) Tumour necrosis factor and other cytokines in murine lupus. *Ann. Rheum. Dis.*, 58(Suppl.):149-55.

Waisman, A. et al. (1993) Variable region sequences of autoantibodies from mice with experimental systemic lupus erythematosus. *Eur. J. Immunol.*, 23:1566-73.

Waisman, A. et al. (1995) The pathogenic human monoclonal anti-DNA that induces experimental systemic lupus erythematosus in mice is encoded by a VH4 gene segment. *Int. Immunol.*, 7:689-696.

Waisman, A., et al. (1997) Modulation of murine systemic lupus erythematosus with peptides based on complementarity determining regions of pathogenic anti-DNA monoclonal antibodies. *Proc. Natl. Acad. Sci. U.S.A.*, 94(4): 4620-5; and.

Zucker, S. et al. (1999) Increased serum stromelysin-1 levels in systemic lupus erythematosus: lack of correlation with disease activity. *J. Rheumatol.*, 26:78-80.

Brosch N. et al. (2000) A Peptide Based on the Sequence of the CDR3 of a Murine Anti-DNA mAb is a Better Modulator of Experimental SLE than its Single Amino Acid-Substituted Analogs. *Cellular Immunology*, 205:52-61.

Brosch N. et al. (2000) Characterization and Role in Experimental Systemic Lupus Erythematosus of T-cell Lines Specific to Peptides Based on Complementarity-Determining Region-1 and Complementarity-Determining Region-3 of a Pathogenic Anti-DNA Monoclonal Antibody. *Immunology* 99:257-264.

Naparstek, Y. et al. (1989) Sequential Anti-Idiotypes Define Reciprocal Idiotopes on the Same Anti-DNA Antibody. *Clinical Immunology and Immunopathology*, 50:S106-S116; and.

Tsokos G.C. et al. (1999) Immune Cell Signaling Defects in Lupus: Activation, Anergy and Death. *Immunology Today*.

\* cited by examiner

PARENTERAL FORMULATIONS OF A PEPTIDE FOR THE TREATMENT OF SYSTEMIC LUPUS ERYTHEMATOSUS

This application claims the benefit of U.S. Provisional Application No. 60/439,950, filed Jan. 14, 2003, the entire contents of which are hereby incorporated by reference.

Throughout this application, various publications are referenced by full citations. The disclosures of these publications in their entireties are hereby incorporated by reference into this application in order to more fully describe the state of the art as known to those skilled therein as of the date of the invention described and claimed herein.

BACKGROUND OF THE INVENTION

Systemic lupus erythematosus (SLE), or lupus, is a debilitating autoimmune disease characterized by the presence of an array of autoantibodies, including antibodies to dsDNA, to nuclear antigens and to ribonucleoproteins. SLE affects approximately 1 in 2000 individuals (U.S. 1 in 700 women). The disease primarily affects young women, with a female-to male ratio of approximately 9:1.

Systemic lupus can affect almost any organ or system of the body. Systemic lupus may include periods in which few, if any, symptoms are evident ("remission") and other times when the disease becomes more active ("flare"). Most often when people mention "lupus," they are referring to the systemic form of the disease.

Corticosteroids are the mainstay in treating systemic autoimmune disorders. Life threatening, severely disabling manifestations of SLE are treated with high doses of glucocorticoids (1-2 mg/kg/day). Undesirable effects of chronic glucocorticoids include an array of prominent adverse effects such as cushingoid habitus, central obesity, hypertension, infection, capillary fragility, hirsutism, accelerated osteoporosis, cataracts, diabetes mellitus, myopathy and psychosis. In addition to corticosteroid toxicity, patient compliance to a dosage regimen also poses a serious problem.

Cytotoxic agents are also used for controlling active disease, reducing the rate of disease flares, and reducing steroid requirements. Undesirable side effects of the latter include bone marrow depression, increased infections with opportunistic organisms, irreversible ovarian failure, alopecia and increased risk of malignancy.

SLE is an inflammatory disease for which to date there is no definitive treatment or cure. The disease results in acute and chronic complications. The only treatments available are palliative, aimed at relieving acute symptoms and preventing chronic complications, often with profound side effects. There is therefore an unmet need in this field, and both physicians and patients would welcome new treatments which could potentially eliminate or reduce the unwanted manifestations of the disease.

Peptides based on the complementarity-determining region of the human monoclonal anti-DNA 16/6Id antibody capable of immunomodulating SLE associated responses have been disclosed in PCT International Publication No. WO 02/067848 A2, the entire contents of which are hereby incorporated by reference. In particular, region CDR1 was found to inhibit the proliferative response of peripheral blood lymphocytes (PBL) of SLE patients to the human anti-DNA 16/6Id mAB, and to ameliorate disease manifestations of mice afflicted with spontaneous or experimental SLE.

Human CDR1, Shown in FIG. 1, is a synthetic peptide of 19 amino acids based on the complementarity-determining region (CDR1) of the human anti-dsDNA mAb denoted 16/6 Id, (SEQ ID NO: 1) (Waisman, A., et al. "Modulation of murine systemic lupus erythematosus with peptides based on complementarity determining regions of pathogenic anti-DNA monoclonal antibodies." *Proc. Nati. Acad. Sd. U.S.A.* (1997), 94(4):4620-4625.

In experimental SLE models—Balb/c mice and SLE-prone mice, i.e. (NZBxNZW)F1 mice—treatment with either mCDR based-peptides or Compound 1 significantly reduced the SLE related findings, notably immune complex deposits (ICD) in the kidney, proteinuria and leukopenia. The treatment had no effect on the 16/6 Id specific antibody response (Waisman, A., et al. "Modulation of murine systemic lupus erythematosus with peptides based on complementarity determining regions of pathogenic anti-DNA monoclonal antibodies." *Proc. Natl. Acad. Sci. U.S.A.* (1997), 94(4): 620; Eilat, E., et al., "Prevention of systemic lupus erythematosus-like disease in (NZBxNZW)F1 mice by treating with CDR1- and CDR3-based peptides of pathogenic autoantibody" *J. Clin. Immunol.* (2000), 20: 268; Eilat, E., et al., "The mechanism by which a peptide based on complementarity determining region-1 of pathogenic anti-DNA antibody ameliorates experimental SLE" (2001), *Proc. Natl. Acad. Sci. U.S.A.* 98: 1148).

These peptides, like many peptides, are not very soluble.

Therefore, formulations that improve the solubility of the peptides are desired.

SUMMARY OF INVENTION

The subject invention provides a pharmaceutical composition comprising
an aqueous carrier;
from 0.1 mg/ml to 20 mg/ml of the composition of a pharmaceutically acceptable salt of a peptide having the structural formula $NH_2$-Gly Tyr Tyr Trp Ser Trp Ile Arg Gln Pro Pro Gly Lys Gly Glu Glu Trp Ile Gly-$COOH$ (SEQ ID NO:1);and a substituted β-cyclodextrin in an amount effective to dissolve the peptide in the aqueous carrier, wherein the composition has a pH between 4 and 9.

The subject invention also provides a pharmaceutical composition comprising
an aqueous carrier;
from 0.1 mg/ml to 20 mg/ml of the composition of an acetate salt of a peptide having the structural formula $NH_2$-Gly Tyr Tyr Trp Ser Trp Ile Arg Gln Pro Pro Gly Lys Gly Glu Glu Trp Ile Gly-$COOH$ (SEQ ID NO:1);

and
from 70 mg/ml to 170 mg/ml of the composition of hepta-(sulfobutyl ether)-β-cyclodextrin,
wherein the peptide and the hepta-(sulfobutyl ether)-β-cyclodextrin are dissolved in the aqueous carrier; and
wherein the solution has a pH between 6.5 and 8.5.

The subject invention also provides a method of alleviating symptoms of systemic lupus erythematosus (SLE) in a human subject comprising administering to the human subject any of the above pharmaceutical compositions in an amount effective to alleviate the symptoms of SLE in the human subject.

The subject invention also provides a process for manufacturing the above pharmaceutical composition comprising the steps of:

a) preparing a solution of a substituted β-cyclodextrin in an aqueous carrier at a predetermined concentration;
b) adding predetermined amount of a pharmaceutically acceptable salt of the peptide NH$_2$-Gly Tyr Tyr Trp Ser Trp Ile Arg Gln Pro Pro Gly Lys Gly Glu Glu Trp Ile Gly-COOH (SEQ ID NO:1) to the solution of step a);
c) adjusting the pH of the solution of step b) until the peptide dissolves in the solution; and
d) if necessary, adjusting the pH of the solution of step c) to a pH of 4-9, thereby manufacturing the pharmaceutical composition.

The subject invention also provides a process of lyophilizing the above pharmaceutical composition, comprising the steps of:
a) lowering the temperature of the pharmaceutical composition to −40° C.;
b) holding the temperature at −40° C. for a predetermined time;
c) raising the temperature of the solution to 20° C.;
d) holding the temperature at 20° C. for a predetermined time; and
e) reducing the pressure to 10 μbar, thereby lyophilizing the pharmaceutical composition.

The subject invention also provides a process of lyophilizing the above pharmaceutical composition, comprising the steps of:
a) lowering the temperature of the pharmaceutical composition to −45° C.;
b) holding the temperature at −45° C. for a predetermined time;
c) raising the temperature of the solution to −20° C.;
d) raising the temperature of the solution to 25° C.; and
e) holding the temperature at 25° C. for a predetermined time, thereby lyophilizing the pharmaceutical composition.

■—Compound 1 (RS) 50 μg/mouse

▲—Compound 1 (RS) 200 μg/mouse

□—DP 50 μg/mouse

Δ—DP 200 μg/mouse

●—12% Captisol® ampulized

Figure 3:
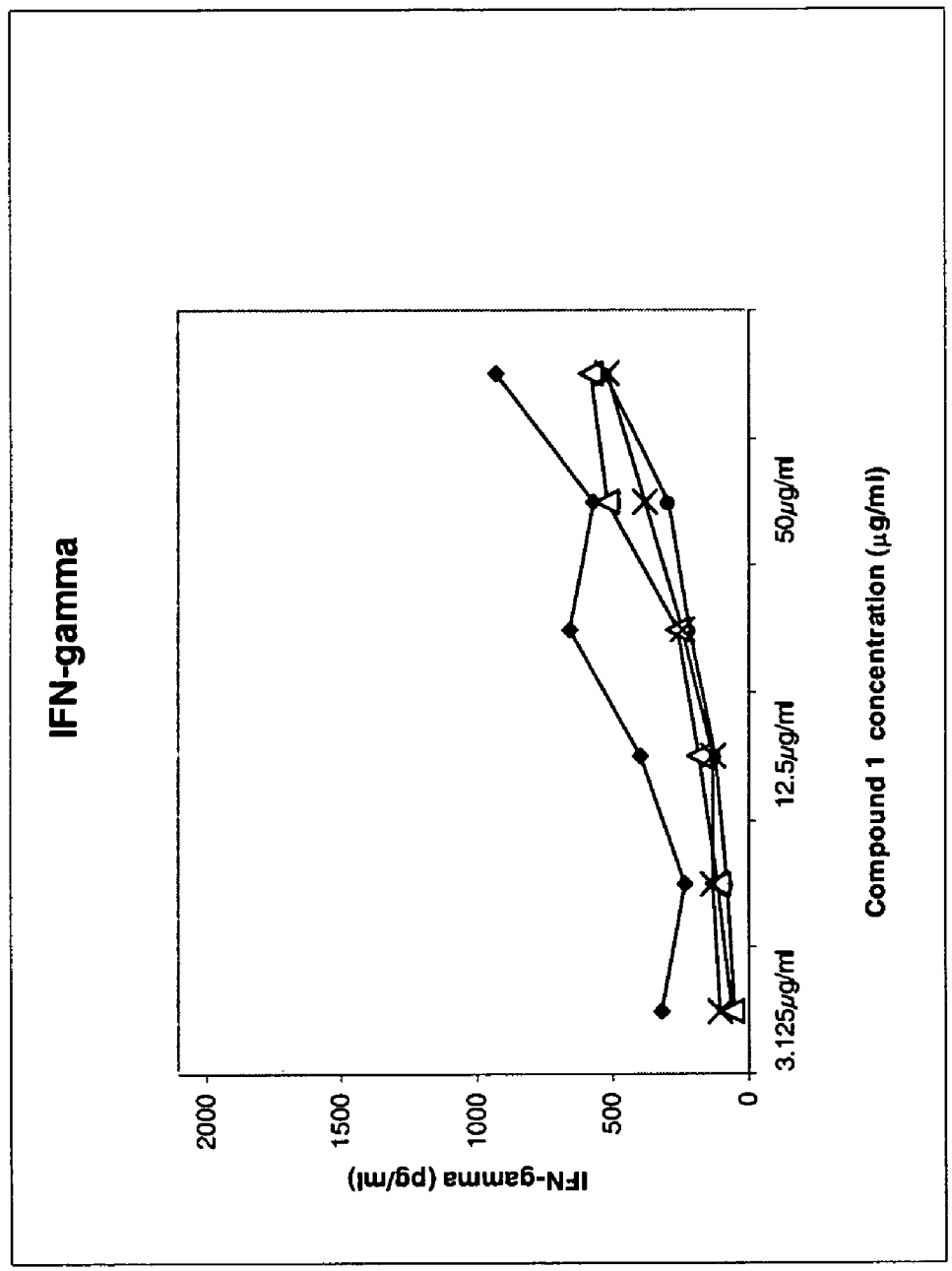

FIG. 3. IFN-γ Secretion from cells taken from mice treated with Compound 1 solution after the cells were subsequently activated with a solution of compound 1 in EM-1 (2.5×10$^6$ cells/well).

♦—Placebo

●—Compound 150 μg/mouse (treatment dose)

Δ—Compound 1100 μg/mouse (treatment dose)

X—Compound 1200 μg/mouse (treatment dose)

Figure 4:
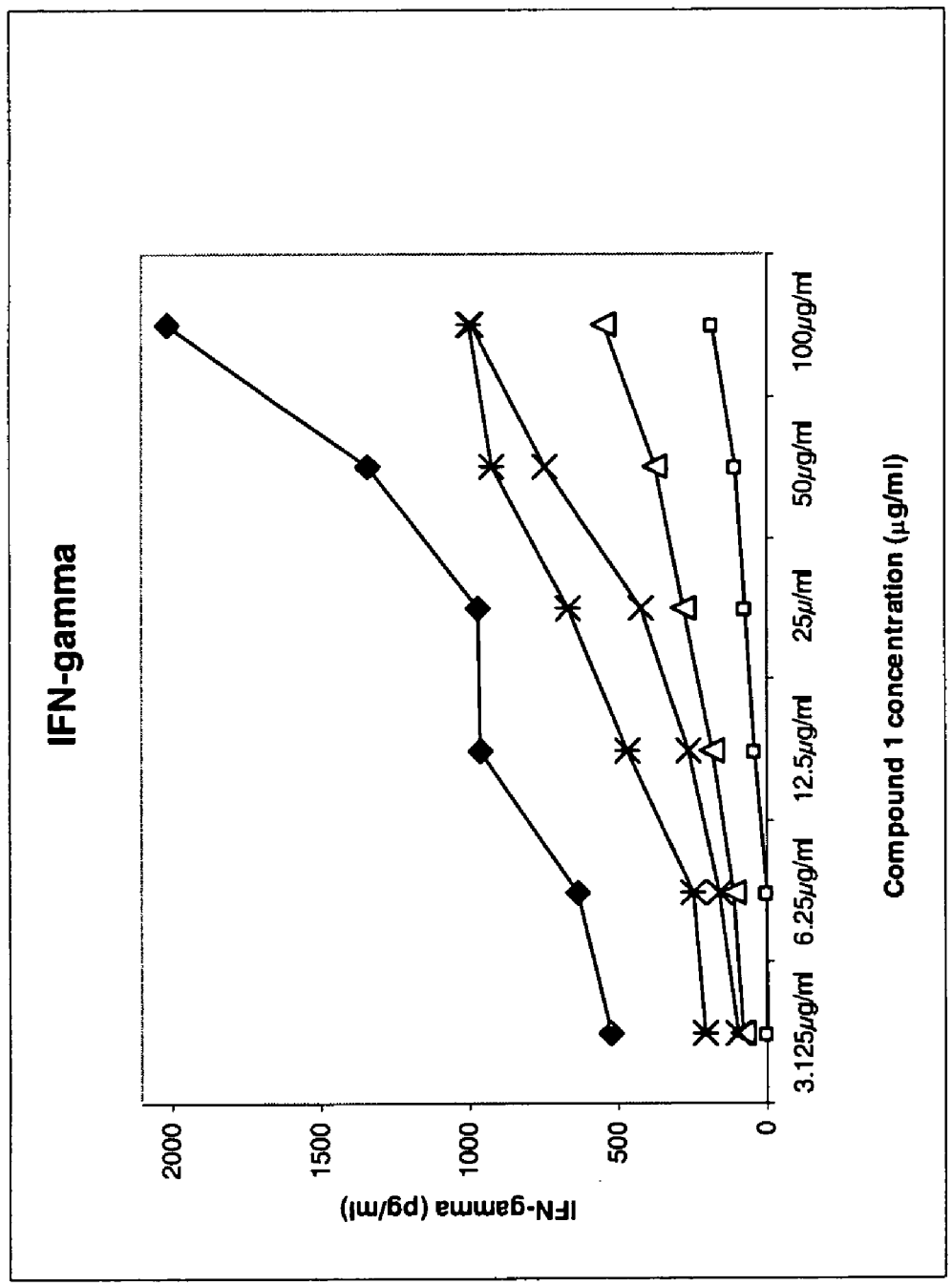

FIG. 4. IFN-γ Secretion from cells taken from mice treated with Compound 1 solution after the cells were subsequently activated with a solution of compound 1 in EM-1 (5×10$^6$ cells/well).

♦—Placebo

□—Compound 125 μg/mouse

Δ—Compound 150 μg/mouse

X—Compound 1100 μg/mouse

*—Compound 1200 μg/mouse

Figure 5:
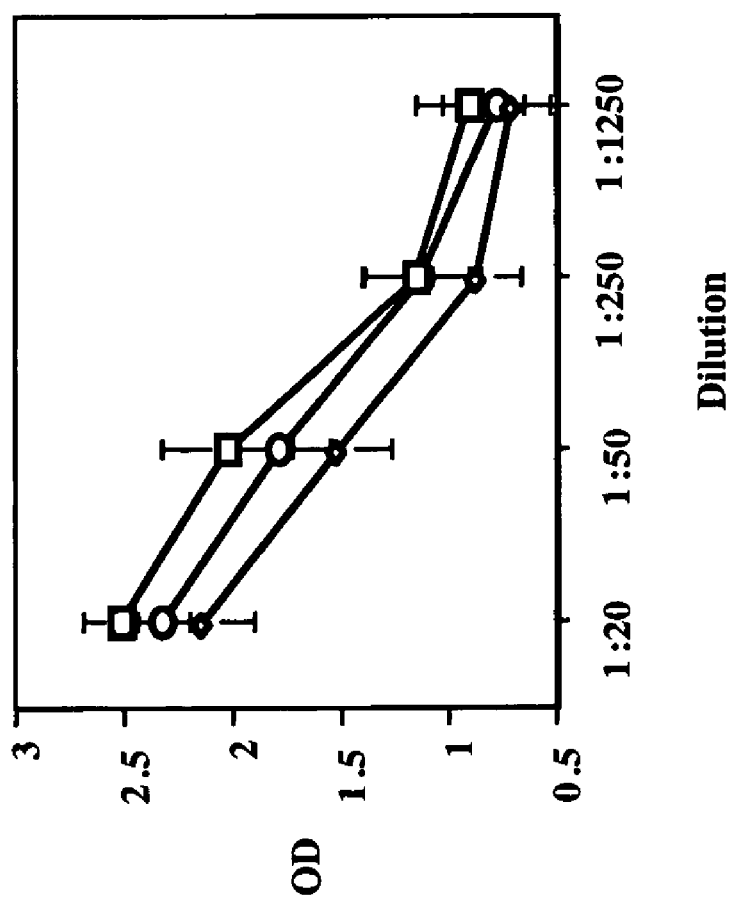

FIG. 5. Anti-dsDNA antibodies in (NZBxNZW)F1 mice after 10 injections with Compound 1 in Captisol® [OD=Optical Density; Compound 1 (C)=Compound 1 dissolved in Captisol®]

□—Placebo

◊—Compound 150 μg/mouse

○—Compound 125 μg/mouse

Figure 6:
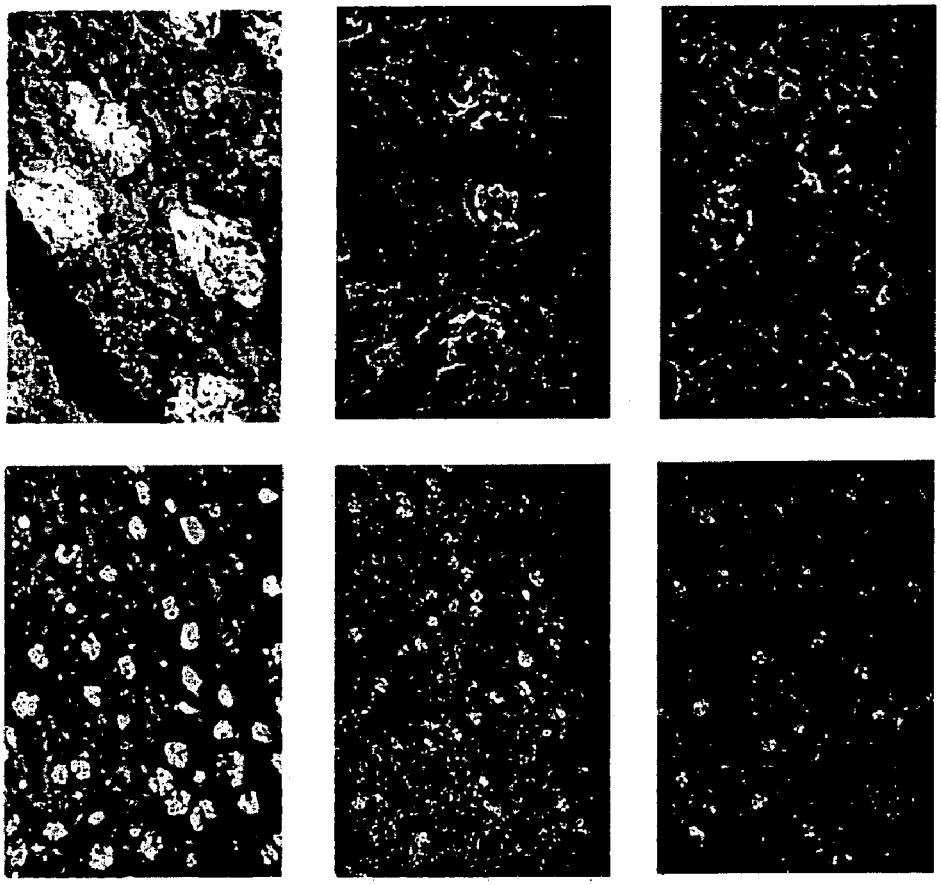

FIG. 6. Kidney sections from (NZBxNZW)F1 mice showing intensity of Immune Complex Deposits. The top row sections are from a Captisol®-treated mouse, the mid-row sections are from a mouse treated with 50 μg/mouse Compound 1 and the bottom row sections are from a mouse treated with 25 μg/mouse Compound 1. Magnification: Left: ×100, Right: ×400. FITC immunohistology.

DETAILED DESCRIPTION

The subject invention provides a pharmaceutical composition comprising
an aqueous carrier;
from 0.1 mg/ml to 20 mg/ml of the composition of a pharmaceutically acceptable salt of a peptide having the structural formula

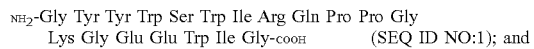
NH$_2$-Gly Tyr Tyr Trp Ser Trp Ile Arg Gln Pro Pro Gly Lys Gly Glu Glu Trp Ile Gly-COOH     (SEQ ID NO:1); and a substituted β-cyclodextrin in an amount effective to dissolve the peptide in the aqueous carrier,
wherein the composition has a pH between 4 and 9.

In one embodiment, the concentration of the acetate salt of the peptide is at least 0.5 mg/ml.

In one embodiment, the concentration of the salt of the peptide is from 0.5 mg/ml to 10 mg/ml.

In another embodiment, the concentration of the salt of the peptide is from 0.5 mg/ml to 2.5 mg/ml.

In another embodiment, the concentration of the salt of the peptide is from 2.5 mg/ml to 5 mg/ml.

In another embodiment, the concentration of the salt of the peptide is from 5 mg/ml to 7 mg/ml.

In another embodiment, the concentration of the salt of the peptide is from 7 mg/ml to 8.5 mg/ml.

In another embodiment, the concentration of the salt of the peptide is from 8.5 mg/ml to 10 mg/ml.

In another embodiment, the concentration of the salt of the peptide is from 9 mg/ml to 10 mg/ml.

In another embodiment, the concentration of the salt of the peptide is from 10 mg/ml to 15 mg/ml.

In another embodiment, the concentration of the salt of the peptide is from 15 mg/ml to 20 mg/ml.

In another embodiment, the concentration of the salt of the peptide is 1.0 mg/ml.

In another embodiment, the concentration of the salt of the peptide is 2.5 mg/ml.

In another embodiment, the concentration of the salt of the peptide is 5 mg/ml.

In another embodiment, the concentration of the salt of the peptide is 10 mg/ml.

In another embodiment, the concentration of the salt of the peptide is 15 mg/ml.

In another embodiment, the concentration of the salt is from 0.1 mg/ml to 0.5 mg/ml.

In another embodiment, the concentration of the salt is from 0.1 mg/ml to 0.2 mg/ml.

In another embodiment, the concentration of the salt is from 0.2 mg/ml to 0.3 mg/ml.

In another embodiment, the concentration of the salt is from 0.3 mg/ml to 0.4 mg/ml.

In another embodiment, the concentration of the salt is from 0.4 mg/ml to 0.5 mg/ml.

In a further embodiment, the composition has a pH between 6.5 and 8.5.

In a further embodiment, the composition has a pH between 7.5 and 8.5.

In a further embodiment, the composition has a pH between 4 and 5.

In a further embodiment, the composition has a pH between 5 and 6.

In a further embodiment, the composition has a pH between 6 and 7.

In a further embodiment, the composition has a pH between 7 and 8.

In a further embodiment, the composition has a pH between 8 and 9.

In another embodiment, the pharmaceutically acceptable salt is an acetate salt.

In another embodiment, the substituted β-cyclodextrin is a hydroxypropyl, a sulfobutyl ether, or a sulfopropyl ether substituted β-cyclodextrin.

In a further embodiment, the substituted β-cyclodextrin is a sulfobutyl ether substituted β-cyclodextrin.

In a further embodiment, the pharmaceutically acceptable salt is an acetate salt, and the substituted β-cyclodextrin is hepta-(sulfobutyl ether)-β-cyclodextrin.

In another embodiment, the composition further comprises a pharmaceutically acceptable buffer in an amount and of a type suitable to make the pH of the pharmaceutical composition in the range of 4-9. The buffer may be acetate buffer, citrate buffer, or sodium carbonate.

The subject invention also provides a pharmaceutical composition comprising an aqueous carrier;

from 0.1 mg/ml to 20 mg/ml of the composition of an acetate salt of a peptide having the structural formula NH₂-Gly Tyr Tyr Trp Ser Trp Ile Arg Gln Pro Pro Gly Lys Gly Glu Glu Trp Ile Gly-COOH (SEQ ID NO:1);

and from 70 mg/ml to 170 mg/ml of the composition of hepta-(sulfobutyl ether)-β-cyclodextrin, wherein the peptide and the hepta-(sulfobutyl ether)-β-cyclodextrin are dissolved in the aqueous carrier; and wherein the composition has a pH between 6.5 and 8.5.

In one embodiment, the concentration of the acetate salt of the peptide is at least 0.5 mg/ml.

In one embodiment, the concentration of the acetate salt of the peptide is from 0.5 mg/ml to 10 mg/ml.

In a further embodiment, the concentration of the acetate salt of the peptide is from 0.5 mg/ml to 2.5 mg/ml.

In another embodiment, the concentration of the salt is from 0.1 mg/ml to 0.5 mg/ml.

In another embodiment, the concentration of the salt is from 0.1 mg/ml to 0.2 mg/ml.

In another embodiment, the concentration of the salt is from 0.2 mg/ml to 0.3 mg/ml.

In another embodiment, the concentration of the salt is from 0.3 mg/ml to 0.4 mg/ml.

In another embodiment, the concentration of the salt is from 0.4 mg/ml to 0.5 mg/ml.

In another embodiment, the concentration of the salt of the peptide is from 5 mg/ml to 7 mg/ml.

In another embodiment, the concentration of the salt of the peptide is from 7 mg/ml to 8.5 mg/ml.

In another embodiment, the concentration of the salt of the peptide is from 8.5 mg/ml to 10 mg/ml.

In another embodiment, the concentration of the salt of the peptide is from 9 mg/ml to 10 mg/ml.

In another embodiment, the concentration of the salt of the peptide is from 10 mg/ml to 15 mg/ml.

In another embodiment, the concentration of the salt of the peptide is from 15 mg/ml to 20 mg/ml.

In a further embodiment, the concentration of acetate salt of the peptide is 1.0 mg/ml.

In a further embodiment, the concentration of acetate salt of the peptide is 2.5 mg/ml.

In another embodiment, the concentration of the salt of the peptide is 5 mg/ml.

In another embodiment, the concentration of the salt of the peptide is 10 mg/ml.

In another embodiment, the concentration of the salt of the peptide is 15 mg/ml.

In another embodiment, the concentration of hepta-(sulfobutyl ether)-β-cyclodextrin is 120 mg/ml and the pH of the composition is between 7.5 and 8.5.

The subject invention also provides a method of alleviating symptoms of systemic lupus erythematosus (SLE) in a human subject comprising administering to the human subject any of the above pharmaceutical compositions in an amount effective to alleviate the symptoms of SLE in the human subject.

The subject invention also provides the above pharmaceutical compositions for use in treating SLE in a human subject.

The subject invention also provides a process for manufacturing any of the above pharmaceutical compositions comprising the steps of:

a) preparing a solution of a substituted β-cyclodextrin in an aqueous carrier at a predetermined concentration;

b) adding predetermined amount of a pharmaceutically acceptable salt of the peptide NH₂-Gly Tyr Tyr Trp Ser Trp Ile Arg Gln Pro Pro Gly Lys Gly Glu Glu Trp Ile Gly-COOH (SEQ ID NO:1) to the solution of step a);

c) adjusting the pH of the solution of step b) until the peptide dissolves in the solution; and d) if necessary, adjusting the pH of the solution of step c) to a pH of 4-9, thereby manufacturing the pharmaceutical composition.

In one embodiment of the process, the resulting final concentration of the substituted β-cyclodextrin in the pharmaceutical composition is from 70 mg/ml to 170 mg/ml.

In one embodiment of the process, the predetermined concentration of the substituted β-cyclodextrin is such which results in a final concentration of substituted β-cyclodextrin in the pharmaceutical composition of from 80 mg/ml to 170 mg/ml.

In one embodiment of the process, the predetermined concentration of the substituted β-cyclodextrin is such which results in a final concentration of substituted β-cyclodextrin in the pharmaceutical composition of from 90 mg/ml to 170 mg/ml.

In one embodiment of the process, the predetermined concentration of the substituted β-cyclodextrin is such which results in a final concentration of substituted β-cyclodextrin in the pharmaceutical composition of from 100 mg/ml to 170 mg/ml.

In one embodiment of the process, the predetermined concentration of the substituted β-cyclodextrin is such which results in a final concentration of substituted β-cyclodextrin in the pharmaceutical composition of from 110 mg/ml to 170 mg/ml.

In one embodiment of the process, the predetermined concentration of the substituted β-cyclodextrin is such which results in a final concentration of substituted β-cyclodextrin in the pharmaceutical composition of from 120 mg/ml to 170 mg/ml.

In one embodiment of the process, the predetermined concentration of the substituted β-cyclodextrin is such which results in a final concentration of substituted β-cyclodextrin in the pharmaceutical composition of from 130 mg/ml to 170 mg/ml.

In one embodiment of the process, the predetermined concentration of the substituted β-cyclodextrin is such which results in a final concentration of substituted β-cyclodextrin in the pharmaceutical composition of from 140 mg/ml to 170 mg/ml.

In one embodiment of the process, the predetermined concentration of the substituted β-cyclodextrin is such which results in a final concentration of substituted β-cyclodextrin in the pharmaceutical composition of from 150 mg/ml to 170 mg/ml.

In one embodiment of the process, the predetermined concentration of the substituted β-cyclodextrin is such which results in a final concentration of substituted β-cyclodextrin in the pharmaceutical composition of from 160 mg/ml to 170 mg/ml.

In one embodiment of the process, the predetermined concentration of the substituted β-cyclodextrin is such which results in a final concentration of substituted β-cyclodextrin in the pharmaceutical composition is 120 mg/ml.

In another embodiment, the predetermined amount of peptide is such which results in a final concentration of peptide in the pharmaceutical composition is at least 0.1 mg/ml.

In another embodiment, the predetermined amount of peptide is such which results in a final concentration of peptide in the pharmaceutical composition is at least 0.5 mg/ml.

In another embodiment, the predetermined amount of peptide is such which results in a final concentration of peptide in the pharmaceutical composition is 2.5 mg/ml, 2.0 mg/ml, 1.0 mg/ml, 0.5 mg/ml or 0.1 mg/ml.

In another embodiment, the predetermined amount of peptide is such which results in a final concentration of peptide in the pharmaceutical composition is 5 mg/ml, 10 mg/ml or 15 mg/ml.

In another embodiment of the process, step b) further comprises mixing the solution for 1 hour.

In another embodiment, in step c) the pH is adjusted using HCl or NaOH 1.0N.

In another embodiment, the process further comprises filtering the solution of step d) through a cellulose acetate filter.

In another embodiment of the above process, the predetermined concentration of the substituted β-cyclodextrin is such which results in a final concentration of substituted β-cyclodextrin in the pharmaceutical composition is 120 mg/ml;

the predetermined amount of peptide is such which results in a final concentration of peptide in the pharmaceutical composition is 2.5 mg/ml, 2.0 mg/ml, 1.0 mg/ml, 0.5 mg/ml or 0.1 mg/ml;

step b) further comprises mixing the solution for 1 hour; and in step c) the pH is adjusted using HCl or NaOH 1.0N, and the process further comprises filtering the solution of step d) through a cellulose acetate filter.

The subject invention also provides a composition prepared by the above process.

The subject invention also provides a process of lyophilizing the above pharmaceutical composition, comprising the steps of:

a) lowering the temperature of the pharmaceutical composition to −40° C.;
b) holding the temperature at −40° C. for a predetermined time;
c) raising the temperature of the solution to 20° C.;
d) holding the temperature at 20° C. for a predetermined time; and
e) holding the temperature at 25° C. for a predetermined time, thereby lyophilizing the pharmaceutical composition.

In one embodiment of the process, step a) is performed within 2 hours.

In another embodiment, step b) is performed within 3 hours.

In a further embodiment, step c) is performed over 13 hours.

In a further embodiment, step c) is performed at a pressure of 110 μbar.

In a further embodiment, step d) is performed over 13 hours.

In a further embodiment, step d) is performed at a pressure of 110 μbar.

In a further embodiment, in step e) the pressure is reduced to 10 μbar.

In a further embodiment, step e) is performed over 5 hours.

In another embodiment of the process,
step a) is performed within 2 hours;
step b) is performed within 3 hours;
step c) is performed over 13 hours and at a pressure of 110 μbar;
step d) is performed over 13' hours and at a pressure of 110 μbar; and
step e) is performed over 5 hours and the pressure is reduced to 10 μbar.

The subject invention also provides a lyophilized pharmaceutical composition prepared by the above process.

The subject invention also provides a process of lyophilizing the above pharmaceutical composition, comprising the steps of:

a) lowering the temperature of the pharmaceutical composition to −45° C.;
b) holding the temperature at −45° C. for a predetermined time;
c) raising the temperature of the solution to −20° C.;
d) raising the temperature of the solution to 25° C.; and
e) holding the temperature at 25° C. for a predetermined time, thereby lyophilizing the pharmaceutical composition.

In one embodiment, step a) is performed within 6 hours.

In another embodiment, step b) is performed within 3 hours.

In another embodiment, step c) is performed over 19 hours.

In another embodiment, step c) is performed at a pressure of 150 μbar.

In another embodiment, step d) is performed over 13 hours.

In another embodiment, step d) is performed at a pressure of 150 μbar.

In another embodiment, step e) is performed over 8 hours.

In another embodiment, step e) is performed at a pressure of 150 μbar.

In another embodiment of the process, step a) is performed within 6 hours;

step b) is performed within 3 hours;

step c) is performed over 19 hours and at a pressure of 150 μbar;

step d) is performed over 13 hours and at a pressure of 150 μbar; and step e) is performed over 8 hours and at a pressure of 150 μbar.

The subject invention also provides a lyophilized pharmaceutical composition prepared by any of the above processes.

In one embodiment of the above lyophilized pharmaceutical composition, the water content of the composition is less than 5%.

In another embodiment, the water content of the composition is less than 4.0%.

In another embodiment, the water content of the composition is less then 3.5%.

The subject invention also provides a lyophilized pharmaceutical composition comprising a pharmaceutically acceptable salt of a peptide having the structural formula NH$_2$-Gly Tyr Tyr Trp Ser Trp Ile Arg Gln Pro Pro Gly Lys Gly Glu Glu Trp Ile Gly-COOH (SEQ ID NO:1); and a substituted β-cyclodextrin.

The subject invention also provides a packaged pharmaceutical composition comprised of:

a packaging material; and a predetermined amount of the above lyophilized pharmaceutical composition.

The preparations of the present invention may be given parenterally, topically, or rectally. They are of course given by forms suitable for each administration route. For example, they are administered by injection, inhalation, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Details of general formulation procedures and information on additional excipients may be found in *Remington: The Science and Practice of Pharmacy*, 20$^{th}$ Edition.

This invention will be better understood from the Experimental Details which follow. However, one skilled in the art will readily appreciate that the specific methods and results discussed are merely illustrative of the invention as described more fully in the claims which follow thereafter.

Experimental Details

EXAMPLE 1

Formulation Development for Compound 1

The human hCDR1 peptide (Compound 1) is described in PCT International Publication No WO 02/067848, published Sep. 6, 2002, and can be prepared by methods well known in the art, (see, for example, *Peptides: Synthesis, Structure and Applications*, ed. by B. Gutte, Academic Press, 1995; *Peptide Synthesis Protocols*, ed. By M. Pennington and B. Dunn, Humana Press, 1994; Schnolzer, M. et al., "In situ neutralization in Boc-chemistry solid phase synthesis. Rapid, High yield assembly of difficult sequences." *Int. J. Pept. Protein Res.* (1992) 40: 180-193).

Figure 1:
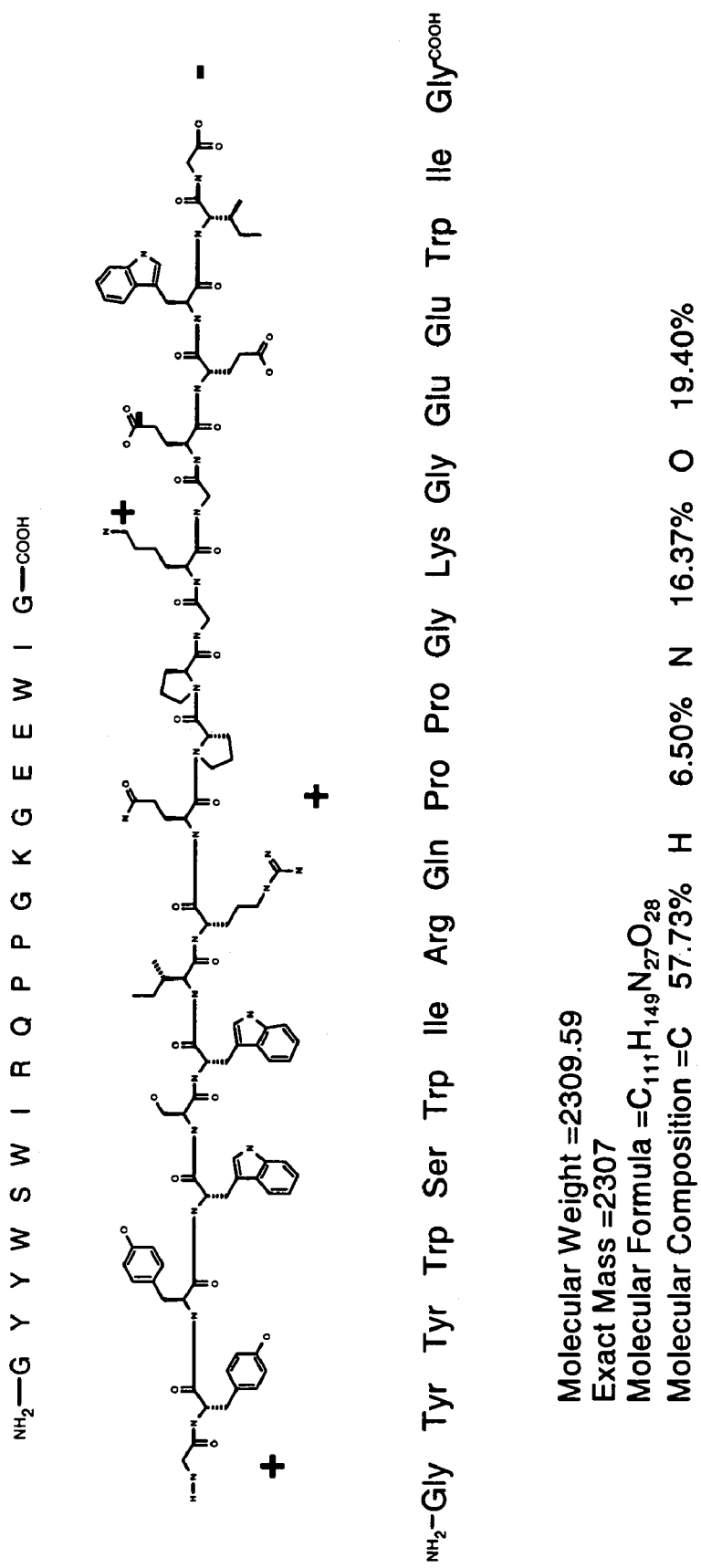
FIG. 1. Human CDR1 (Compound 1) as acetate salt - showing the molecular and structural formulas of hCDR1, the amino acid sequence, (SEQ ID NO: 1) and physical parameters.

Compound 1 is a synthetic polypeptide composed of 19 amino acids. It is provided as an acetate salt. The aqueous solubility of the peptide has been determined to be less than 0.5 mg/ml. FIG. 1 shows compound 1 as an acetate salt.

In order to develop a formulation with peptide concentration exceeding 2 mg/ml, preferably up to 10 mg/ml, experiments with several solubility enhancers were performed. The preliminary experiments indicated that a concentration of 2 mg/ml cannot be easily attained. In order to develop a formulation for sub-cutaneous injection, it is also desirable that the pH be in the range of 4 to 9 and that the solution be iso-osmotic.

Based on an extensive literature survey, a few principal approaches were adopted in order to produce a formulation with maximal solubility. The factors considered were:

pH adjustment and buffers

Solvents

Co-solvents

Solubilizing agents

Methods

Compound 1 was dissolved in the chosen solubility enhancer solution either separately or in combination with other excipients and the solutions were stirred for at least an hour. The pH was adjusted if needed. The solutions were visually examined to estimate the solubility and sent for analytical assay determination. For a few chosen formulations, biological activity was also tested.

Results

Table 1 presents the type of solubility enhancers used for the formulation development. Tables 2 and 3 summarize the experiments that were performed with the various solubility enhancers. Table 2 summarizes the initial screening performed with peptide concentrations in the range of 5 to 10 mg/ml. The experimental work that was performed with higher peptide concentration was then repeated with the lower doses (see table 3)

Initial tests indicated that Compound 1 was more soluble at the limits of the desired pH levels, both acidic and basic, but was less stable at the basic pH range. Thus, several buffers and pH adjustment agents were tested, including acetate buffer, citrate buffer and sodium carbonate. None of the initially tested buffers achieved the desired peptide solubility level. Only above pH 9.2 and below pH 3.0 were solubility levels of 2 mg/ml observed. Nevertheless, at the initial stage, formulations with acetate buffer and citrate buffer (with Mannitol as a tonicity agent) were selected for initial toxicology studies. These formulations were tested for biological activity and proven active.

Non aqueous solvents (see table 1) such as Ethanol, Glycerin, Propylene glycol, Chremophore and their combinations were tested but did not increase the solubility of Compound 1. A solution of 30% DMA (dimethyl-acetamide) yielded solubility in the desired ranges (5 to 9 mg/ml), but was not suitable for a pharmaceutical formulation due to its toxicity profile. Improved solubility was also observed using 30% (w/w) PEG 400 (5 to 9 mg/ml). This latter formulation was chosen for the toxicology studies, but it has proved to be both inactive in the biological assay, and may have been the cause of some adverse effects in a mouse toxicity study. Thus, it was decided not to further pursue this formulation. In view of the preliminary experiments non-aqueous solvents were not used in the subject formulations.

Several amino acids (see table 1) including L-Arginine, L-Glutamic acid, L-Glycine and L-Lysine were tested to improve the protein solubility. The solubility of the peptide in L-Arginine was at the desired level but the resulting pH was above 9. An attempt to decrease the pH or use an Arginine HCl salt resulted in precipitation of the peptide. Human Serum Albumin was also tested and improved the solubility of the peptide at low peptide concentrations (1 mg/ml) (see table 3). However, due to its potential immunogenicity and the low peptide solubility, it was not utilized in further experiments.

Bulking agents (see table 1) including Mannitol, Sorbitol and Dextran were tested alone and in combination with other excipients, but did not improve the solubility of the peptide in solution.

Co-solvents (see table 1), including Polysorbate 20 and Polysorbate 80 were tested alone and in combination with other excipients. While lower concentrations of Polysorbates (up to 6%) did not improve the solubility of the peptide, higher concentrations (up to 10%—see table 2) improved the solubility of the peptide up to 2 mg/ml. However, such high concentrations of Polysorbates were deemed unsuitable for pharmaceutical formulations.

Two types of cyclodextrins, both approved for use in marketed parenteral products, were also tested: Hydroxypropyl-β-cyclodextrin and Sulfobutylether-β-cyclodextrin (Captisol®). Both markedly increased the solubility of the peptide (concentrations in the levels of 10 mg/ml for Hydroxypropyl-β-cyclodextrin and 2.5 for Captisol®). The biological activity of the two cyclodextrin formulations was tested and was found to be equal to the activity of the peptide alone.

CAPTISOL® is a commercially available polyanionic β-cyclodextrin derivative with a sodium sulfonate salt separated from the hydrophobic cavity by a butyl ether spacer group, or sulfobutylether (SBE). CAPTISOL® is the trade name for CyDex Inc.'s hepta-substituted sulfobutylether β-cyclodextrin (SBE7-β-CD) preparation (captisol.com). The structure of CAPTISOL® allows drug molecules to fit in the hydrophobic cavity, thereby isolating the drug molecule from the aqueous solvent. Because the outer surface of CAPTISOL® is hydrophilic, the solubility of the complexed drug molecule is thereby enhanced. The use of cyclodextrins to enhance the solubility of drug molecules is disclosed in U.S. Pat. Nos. 5,134,127 and 5,376,645, the entire contents of which are hereby incorporated by reference.

According to the literature of CyDex Inc., CAPTISOL® is safe when administered parenterally and does not exhibit the nephrotoxicity associated with beta-cyclodextrin. Relative to beta-cyclodextrin, CAPTISOL® provides comparable or higher complexation characteristics and superior water solubility in excess of 90 grams/100 ml—a 50-fold improvement.

Conclusions

Several solubility enhancers were found to match the desired solubility range: DMA, PEG-400, dimethyl-acetamide, polyethylene glycol, polyoxylated castor oil, N-methyl-2-pyrrolidinone, 1-ethenyl-2-pyrrolidinone, Polysorbate 20, Polysorbate 80, Hydroxypropyl-α-cyclodextrin and Sulfobutylether-β-cycldextrin (Captisol®). Of these solubility enhancers both cyclodextrins have proven to be superior with respect to solubility, biological activity and stability. Thus, it was decided to select Captisol® as the solubility enhancer for use in Example 5 formulations and to further study both cyclodextrin formulations. The final formulation for the Example 5 clinical studies consists of: 120 mg/ml of Captisol® in water with the desired amount of peptide (0.5, 1.0 or 2.5 mg/ml), and HCl and NaOH for pH adjustment.

TABLE 1

Solubility enhancers used for Compound 1 formulation development

| Solubility enhancer classification | Solubility Enhancers |
|---|---|
| Solvents | Cremophor EL, CMC, Ethanol, DMA, Gycerin, Propylene Glycol, PEG 400, Monotioglycerol |
| Co-solvents | Polysorbate 20, Ploysorbate 80 |
| Solubilizing agents | Arginine, HSA, Glycine, Creatinine, Glutamic acid, Lysine (acetate salt and free base), Captisol ®, Hydroxypropyl-β-cyclodextrin, |
| Bulking agents | Mannitol, Sorbitol, Dextrose, Lactose Dextran |
| pH Adjustment Agents | Citrate buffer, Acetate buffer, Sodium Carbonate |

TABLE 2

List of Cosolvents and Stabilizers evaluated in Compound 1 Peptide Formulations.

| Solubility Enhancer* | % Used | % of Standard amount from the literature | Amount of peptide added (mg/ml) | Assay, % | pH of formulation | Remarks |
|---|---|---|---|---|---|---|
| Albumin (HSA), Dextrose | 1.5 1.5 | 0.4-5.0 | 5 | — | 6.0 Adjust. to 4.1 | Insoluble |
| Albumin (HSA), Polysorbate 80, Glycine | 1.0 0.6 2.0 | 0.4-5.0 0.8-4.0 0.2-2.1 | 5 | — | 5.8 Adjust. to 4.1 | Insoluble |
| Arginine | 1.5 | 0.8-1.6 | 15 | 93 | 9.8 | Clear solution |
| Arginine HCl | 2.0 | 0.8-1.6 | 5 | — | 3.5 | Insoluble |
| Arginine Lactose | 1.5 1.5 | 0.8-1.6 | 15 | 93 | 9.8 | When the pH was lowered below 8.5 the peptide precipitated and the solution turned into gel |
| Captisol ® | 10.0 20.0 | Up to 30.0 | 10 | 86 89 | 4.9 Adjust. to 4.4 | Turbid solution |
| CMC (carboxy methyl cellulose) in acetate | 0.2 0.05M | | 5 | 90 | 5.0 | For toxicology studies |
| Creatanine | 0.8 | Up to 0.6 | 5 | — | 6.1 Adjust. to 4.1 | Insoluble |
| Cremophor EL Ethanol Dimethylacetamide | 15.0 10.0 6.0 | −10.0 0.6-32.9 0.012-6.0 | 5 | — | 4.0 | Very turbid |
| Dextran | 4.0 to 15.0 | 3.0-30.0 | 5 | — | 3.9 | Insoluble |
| Dimethylacetamide (DMA) | 6.0-20.0 | 0.012-6.0 | 5 | — | 4.6 | Insoluble |
| Dimethylacetamide (DMA) | 25.0 | 0.012-6.0 | 5 | 87 | 5.1 | Clear solution |
| Dimethylacetamide (DMA) | 30.0 | 0.012-6.0 | 10 | 93 | 5.1 | Clear solution |
| Ethanol | 10.0 | 0.6-32.9 | 5 | — | — | Insoluble |
| Glutamic acid | 2.0 | | 5 | — | 3.7 | When the pH was increased above 4 the peptide precipitated and the solution turned into gel |
| Glycerin | 1.5 | 1.6-32.5 | 5 | 37 | 4.5 | Insoluble |
| Glycerin | 30.0 | 1.6-32.5 | 5 | — | 3.7 | Insoluble |
| Glycerin, Polysorbate 80 | 10.0 0.6 | 1.6-32.5 0.8-4 | 5 | 12 | 6.5 Adjust. to 4.5 | Insoluble |
| Glycine | 0.4 | 0.2-2.1 | 5 | — | 4.6 | Insoluble |
| Hydroxypropyl β-cyclodextrin | 20.0 | Up to 30.0 | 10 | 99 | 4.6 | Clear solution |
| Lysine Acetate Salt | 2.0 | | 5 | — | 3.8 | Insoluble |
| Lysine Free base | 2.0 | | 5 | — | 9.2 | When the pH was lowered below 8 the peptide precipitated and the solution turned into gel |
| Mannitol in Citrate buffer | 4.0 0.035M | 2.0-10.0 | 5 | 38 | 3.4 | For toxicology studies |
| Mannitol in acetate buffer | 4.0 0.05M | 2.0-10.0 | 5 | 32 | 4.3 | For toxicology studies |
| Mannitol, Glycine | 20.0 0.4 | 2.0-10.0 0.2-2.1 | 5 | 14 | 6.4 Adjust. to 4.5 | Insoluble |
| Mannitol, Polysorbate 20 | 20.0 0.6 | 2.0-10.0 — | 5 | 22 | 6.5 Adjust. to 4.5 | Insoluble |
| Monothioglycerol | 1.0 | 0.1-10.0 | 5 | — | 4.5 | Turbid solution |
| PEG 400 | 30.0 | Up to 30.0 | 5 | 88 | 4.2 | Slightly opalescent |
| PEG 400 | 30.0 | Up to 30.0 | 10 | 89 | 4.2 | Turbid solution |
| PEG 400 with DMA | 30.0 6.0 | Up to 30.0 0.012-0.6 | 5 | 94 | 4.2 | Clear solution |
| PEG 400 | 10.0 | 6.0-18.0 | 5 | 58 | 4.2 | Insoluble |
| PEG 400 DMA | 10.0 10.0 | Up to 30.0 0.012-0.6 | 5 | — | 4.3 | Insoluble |
| PEG 400 Propylene glycol PG | 10.0 10.0 | Up to 30.0 10.0 | 5 | — | 4.1 | Insoluble |
| PEG 400 Propylene glycol | 18.0 50.0 | Up to 30.0 10.0 | 5 | 100 | 4.2 | Clear solution |
| Polysorbate 80 | 1.6 | 0.8-4.0 | 5 | 24 | 7.2 Adjust. to 4.5 | Insoluble |
| Polysorbate 80 | 6.0 | 0.8-4.0 | 5 | — | 3.9 | Insoluble |
| Polysorbate 80 Creatanine | 6.0 0.6 | 0.8-4.0 up to 0.6 | 5 | — | 4.0 | Insoluble |
| Propylene glycol PG DMA | 10.0 10.0 | 10.0 0.012-0.6 | 5 | — | 4.2 | Insoluble |
| Propylene glycol PG | 10.0, 30.0 | 10.0 | 5 | — | 4.2 | Insoluble |

TABLE 2-continued

List of Cosolvents and Stabilizers evaluated in Compound 1 Peptide Formulations.

| Solubility Enhancer* | % Used | % of Standard amount from the literature | Amount of peptide added (mg/ml) | Assay, % | pH of formulation | Remarks |
|---|---|---|---|---|---|---|
| Sodium Carbonate | 1.5 | | 5 | — | 11.4 | When the pH was lowered below 8.5 the peptide precipitated and the solution turned into gel |
| Sorbitol | 5.0 | 10.0-25.0 | 5 | — | 6.9 Adjust. to 4.5 | Turbid solution |

TABLE 3

Compound 1 formulations at low peptide concentrations

| Solubility Enhancer* | % Used | % of Standard amount from the literature | Amount of peptide added (mg/ml) | Assay, % | pH of formulation | Remarks |
|---|---|---|---|---|---|---|
| Albumin (HSA), | 5.0 | 0.4-5.0 | 1.0 | 90 | 6.9 | Clear solution |
| | | | 2.5 | — | Adjust. to 4.5 | Turbid solution |
| Arginine | 1.5 | 0.8-1.6 | 1.0 | 24 | 10.6 Adjust. to 8.5 | When the pH was lowered below 8.5 the peptide precipitated and the solution turned into gel |
| Captisol ® | 12.0 | Up to 30.0 | 1.0 | 106 | 5.3 | Clear solution |
| | | | 2.5 | 100 | 6.5 to 8.5 | |
| Dextran | 20.0 | 3.0-30.0 | 1.0 | 69 | 4.8 Adjust. to 4.0 | Turbid solution |
| Glycerin | 30.0 | 1.6-32.5 | 1.0 | — | 4.8 Adjust. to 4.0 | Turbid solution |
| Mannitol | 4.0 | 0.8-4.0 | 1.0 | 64 | 4.7 Adjust. to 4.0 | Turbid solution |
| Polysorbate 20 | 10.0 | — | 1.0 | 95 | 5.8 | Clear solution |
| | | | 2.5 | 88 | Adjust. to 4.8 | Clear with small amount of precipitation |
| Polysorbate 20 Mannitol | 10.0 2.0 | — 2.0-10.0 | 2.5 | 115 | 5.1 Adjust. to 4.3 | Clear solution |
| Polysorbate 80 | 4.0 6.0-10.0 | 0.8-4.0 | 1.0 2.5 | 91 89 | 5.5 Adjust. to 5.0 | Clear solution Slightly turbid solution |
| Polysorbate 80 Mannitol | 4.0 2.0 | 0.8-4.0 2.0-10.0 | 2.5 | 88 | 5.1 Adjust. to 4.4 | Slightly turbid solution |
| Propylene glycol PG | 10.0 | 10.0 | 1.0 | 78 | 5.0 Adjust. to 4.4 | Turbid solution |
| Sorbitol | 20.0 | 10.0-25 | 1.0 | 52 | 4.5 | Turbid solution |

EXAMPLE 2

Preparation Protocol for Solution of Compound 1 in Captisol®

Standard dissolution methods, such as mixing dry Compound 1 and dry Captisol® into water or adding Compound 1 to a prepared solution of Captisol® and water did not result in complete dissolution at the desired concentrations. Several different concentrations of both Compound 1 and Captisol® were tested at various pH levels. However, the following method for producing a solution of Compound 1 in Captisol® resulted in complete dissolution at the desired concentrations.

Materials: Captisol®, Compound 1 and water

Method:
1. Weigh the appropriate amount of Captisol® to give a final concentration of 120 mg/ml.
2. Add 80% of the final amount of water and mix for 10 minutes with a magnetic stirrer.
3. Weigh Compound 1 to give a final concentration of 2.5 mg/ml, 2.0 mg/ml, 1.0 mg/ml, 0.5 mg/ml or 0.1 mg/ml.
4. Add the peptide to the Captisol® solution. Mix for 1 hour.
5. Raise the pH to obtain clear solution (in the 2.0 mg/ml formulation there might be a need to raise the pH slightly above 9). pH should be adjusted using HCl 1.0 N and NaOH 1.0 N. Mix for 10 minutes.
6. Correct the pH to the range of 7.5 to 8.5 if needed (using either HCl or NaOH 1.0 N).
7. Add water to final volume.
8. Filter the solution through a 0.2μ cellulose acetate filter.
9. Record final pH.
10. Dispense into aliquots and store at the proper temperature.

EXAMPLE 3

Lyophilization of Compound 1 and Captisol® Solution

The current lyophilization process differs from other lyophilization processes in that the percentage of solids in the formulation is high (12%) whereas lyophilized products normally contain between 5 and 10% solids.

Equipment

The freeze drier used was an Edwards lyophilizer Lyoflex 0.6. The equipment IQ/OQ was performed and checked for compliance by quality assurance prior to the process development.

Solutions of Compound 1 and Captisol® at concentrations of 0.5 mg/ml, 11.0 mg/ml and 2.5 mg/ml of Compound 1 were prepared. The fill-volume was adjusted 1 ml (1.05 gr).

Main Process Steps:
1. Freezing
2. Holding (at low temperature)
3. Drying under vacuum in two stages:
    3.1. Primary drying—shelf warming to an upper hold temperature, controlling shelf temperature at the upper hold level.
    3.2. Secondary drying—Pressure reduction to a minimal value at the upper hold shelf temperature.

Batches 1-3

Freezing—Freezing was from room temperature to −40° C. within 2 hours. Shelves were held at −40° C. for 3 hours.

Drying—Drying was performed at 110 µbar pressure. Shelf temperature was increased to 20° C. over 13 hours and held at that temperature for additional 13 hours.

Total process time was 31 hours.

Results:
Water content results were:
Batch no. 1: 3.8%
Batch no. 2: 4.0% and
Batch no. 3: 4.9%

Batches 4 and 5

Since the water content results of the processes leading to batches 1, 2 and 3 were higher then the desired value, it was decided to add a secondary drying step at the same temperature and at low pressure.

Drying—Drying was performed at 110 µbar pressure. Shelf temperature was increased to 20° C. over 13 hours and held at that temperature for additional 13 hours (Batch 4) or 8 hours (Batch 5). Pressure was decreased to 10 µbar for additional 5 hours.

Total process time was 36 hours.

Results:
Water content results were
Batch 4: Placebo: 3.0%,
1 mg/ml: 3.9%.
Batch 5: Placebo: 4.1%

Conclusions

As shown, a satisfactory lyophilization process for Compound 1 with Captisol® was developed. Due to the high percentage of solids and hence the condensed cake, the developed process is longer then the currently available lyophilization cycles for peptides and it exhibits an additional secondary drying stage.

Table 4 summarizes the developed process.

TABLE 4

| Step | Compound 1 (Peptide) with Captisol ® |
|---|---|
| Loading | 5° C. |
| Freezing | 2 hours to −40° C. |
| Hold at low temp. | 3 hours to −40° C. |
| Primary Drying: | |
| Warm to 20° C. | 13 hours pressure 110 µbar |
| Hold at 20° C. | 13 hours pressure 110 µbar |
| Secondary drying: | |
| Hold at 20° C. | 5 hours pressure 10 µbar |
| Storage at | −20° C. |
| Process time | 36 hours |

EXAMPLE 4

Examination of the In-Vivo Biological Activity of the Lyophilized Compound Solution (DP, 1 mg/Vial, 12% Captisol®)

Figure 2:
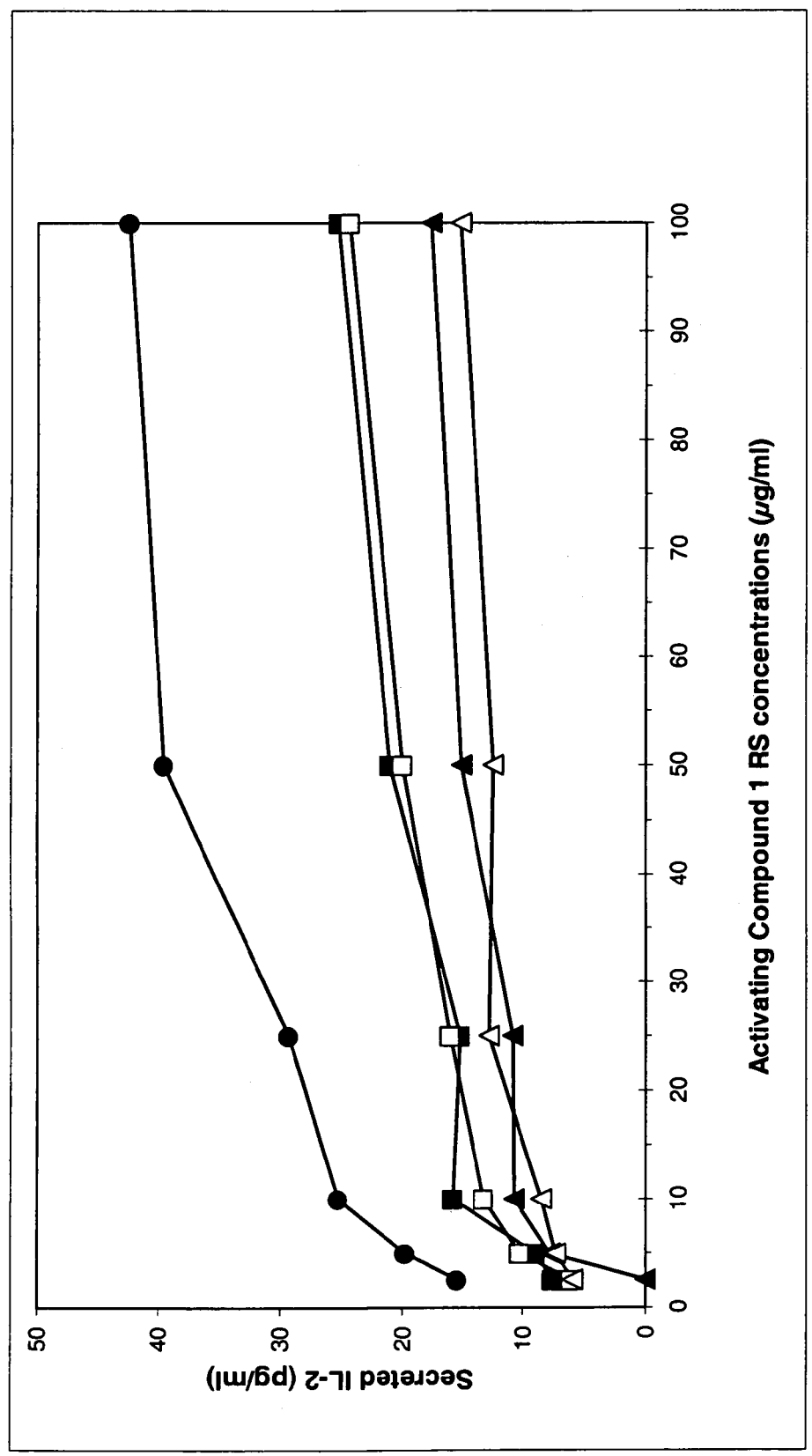
FIG. 2. IL-2 Secretion from cells taken from mice treated with Compound 1 and Captisol® solution after the cells were subsequently activated with a solution of Compound 1 in PBS.

The biological activity was monitored by inhibition of IL-2 secretion from Compound 1 reference standard (RS) specific T-cells following subcutaneous (s.c.) treatment with the lyophilized compound solution, i.e. the drug product (DP), at two concentrations. The results of the treatment are compared to those of treating mice with Compound 1 (RS) in phosphate buffered saline (PBS). The results are shown in the tables below and in FIG. 2.

Experimental Design:

| | | |
|---|---|---|
| 1. Immunization (Compound 1 RS emulsified with CFA, at all four footpads) | | Day 0 |
| 2. Treatment (s.c. at the back of the neck, in 200 µl solution) | | Day 0 |
| 3. In-vitro activation with: a. Compound 1 RS at concentrations of 0; 0.5; 1; 2.5; 5; 10; 25; 50 and 100 µg/ml b. a peptide with the reverse order of amino acids of Compound 1 (negative control). c. Con A (positive control). | | Day 10 |
| 4. Incubation of culture for 20 hrs at 37° C. in a humidified 5% $CO_2$ incubator. | | |
| 5. IL-2 measurement by ELISA. | | |

Table of experimental Groups:

| Group | Immunization with | Treatment |
|---|---|---|
| A | 50 µg Compound 1 RS | 50 µg Compd. 1 RS in PBS |
| B | | 200 µg Compd. 1 RS in PBS |
| C | | 50 µg DP (batch 2) |
| D | | 200 µg DP (batch 2) |
| F | | Placebo (12% captisol ®) |

IL-2 Secretion from Compound 1 (DP) Treated Mice Following In-Vitro Activation with Compound 1 RS (pg/ml)

Treated with:

| | | Group | | | | | | | | |
|---|---|---|---|---|---|---|---|---|---|---|
| | | F | A | | B | | C | | D | |
| Activator | Concentration of activator (μg/ml) | 12% captisol ® Ampulized | Compd. 1 RS 50 μg/ mouse | % inhib. | Compd. 1 RS 200 μg/ mouse | % inhib. | DP 50 μg/mouse | % inhib. | DP 200 μg/mouse | % inhib. |
| Con A | 2.5 | 5,825 | 6,215 | | 5,403 | | 3,537 | | 4,069 | |
| Compd. 1 RS | 0 | BQL | BQL | | BQL | | BQL | | BQL | |
| Compd. 1 RS | 0.5 | 11 | 9 | | 10 | | 8 | | BQL | |
| Compd. 1 RS | 1 | 10 | BQL | | BQL | | BQL | | BQL | |
| Compd. 1 RS | 2.5 | 15 | 8 | 51 | BQL | NA | 6 | 61 | 6 | 62 |
| Compd. 1 RS | 5 | 20 | 9 | 55 | 8 | 60 | 10 | 48 | 7 | 63 |
| Compd. 1 RS | 10 | 25 | 16 | 38 | 11 | 58 | 13 | 48 | 8 | 67 |
| Compd. 1 RS | 25 | 29 | 15 | 48 | 11 | 63 | 16 | 45 | 13 | 56 |
| Compd. 1 RS | 50 | 40 | 21 | 47 | 15 | 62 | 20 | 50 | 12 | 69 |
| Compd. 1 RS | 100 | 42 | 25 | 41 | 18 | 58 | 24 | 43 | 15 | 64 |
| | Average inhibition (%) (at the range of 5-100 μg/ml) | | | 45.6 | | 60.4 | | 46.8 | | 63.7 |

BQL = Below Quantitation Limit
NA = Not Applicable
Rows 1-4 were not included in the curve

EXAMPLE 5

Evaluation of Optimal Dose for Treatment

The following abbreviations are used in the following description:

| | |
|---|---|
| CFA | Complete Freund's adjuvant |
| Con A | Concanavalin A |
| DP | Drug Product |
| DS | Drug Substance |
| EM-1 | Enriched DCCM-1 Medium |
| EM-3 | Enriched RPMI-1640 + fetal calf serum medium |
| FCS | Fetal Calf Serum |
| IFN-γ | Interferon-gamma |
| LN | Lymph Node |
| PBS | Phosphate Buffered Saline |
| RS | Reference Standard |
| s.c. | Subcutaneous |
| TB | Trypan Blue |
| TGF-β | Transforming Growth Factor-beta |
| WFI | Water for Injection |

Introduction

A group of 20 mice were immunized with 50 μg/mouse of Compound 1 RS. The immunized mice were allocated to five treatment groups as follows: placebo, 25, 50, 100 and 200 μg/mouse of Compound 1 DP (subcutaneous administration). Ten days post immunization and treatment, LN was extracted and single cell suspension was prepared. The in-vitro secretion of IFN-γ and TGF-β by the cultured cells in response to activation with several concentrations of Compound 1 RS was then measured.

Experimental Design

| | | |
|---|---|---|
| 1. | Immunization | -Day 0 |
| 2. | Treatment with Compound 1 DP | -Day 0 |
| 3. | In-vitro activation of LN cells from treated mice | -Day 10 |
| 4. | Collection of culture media (for IFN-γ determination) | -Day 12 |
| 5. | Collection of culture media (for TGF-β determination) | -Day 13 |
| 6. | ELISA for IFN-γ | |
| 7. | ELISA for TGF-β | |

TABLE 7

Experimental Groups

| | | | | In-vitro activation | |
|---|---|---|---|---|---|
| Exp. Group | Treatment Article | Mice/group | Cells/well | Compound 1 RS concentration | |
| A1 | Control 12% Captisol ® | 4 | $2.5 \times 10^6$ $5 \times 10^6$ | Compound 1 RS 0-100 μg/ml | |
| A2 | 25 μg/mouse | 4 | $2.5 \times 10^6$ $5 \times 10^6$ | | |
| A3 | 50 μg/mouse | 4 | $2.5 \times 10^6$ $5 \times 10^6$ | | |
| A4 | 100 μg/mouse | 4 | $2.5 \times 10^6$ $5 \times 10^6$ | | |
| A5 | 200 μg/mouse | 4 | $2.5 \times 10^6$ $5 \times 10^6$ | | |

Materials and Reagents

Animals

Mice: 20 female BALB/c mice, supplied by Harlan animals breeding center, Rehovot.
Age at immunization (week+days): 10
Average weight of mice included in the experiment: 19.01 gr.

Materials

General Reagents

70% ethanol was prepared from 96% ethanol by diluting with purified $H_2O$.

Preparation of Compound 1 Solutions for Immunization

CFA-Compound 1 RS emulsion (500 µg/ml, 50 µg/mouse) was prepared as follows:
1. 1.874 mg of Compound 1 was dissolved in 1.87 ml of WFI to yield a solution of 1 mg/ml.
2. The solution was tested with a pH indicator strip and found to have a pH of 5.
3. 1.5 ml of the solution were emulsified with 1.5 ml CFA resulting in a final concentration of 500 µg/ml.

Preparation of Solutions for Treatment

Treatment was by a s.c. injection of 200 µl solution.

Preparation of 12% Captisol® Solution 1.2 gr of captisol® were dissolved in 10 ml of WFI to yield a solution of 12% captisol®.

Experimental Procedure

Mice Weighing

Mice were weighed before immunization. Average mice weight: 19.01±0.97 gr

TABLE 8

The in-vitro experimental groups

| Experimental Group | Treatment Article | Cells/well | In-vitro activation Activation substance concentration |
|---|---|---|---|
| A1-2.5 | Control | $2.5 \times 10^6$ | Compound 1 RS |
| A1-5 | 12% Captisol® | $5 \times 10^6$ | 0; 3.125; 6.25; 12.5; 50 and 100 µg/ml |
| A2-2.5 | DP | $2.5 \times 10^6$ | Con A 2.5 µg/ml |
| A2-5 | 25 µg/mouse | $5 \times 10^6$ | |
| A3-2.5 | DP | $2.5 \times 10^6$ | |
| A3-5 | 50 µg/mouse | $5 \times 10^6$ | |
| A4-2.5 | DP | $2.5 \times 10^6$ | |
| A4-5 | 100 µg/mouse | $5 \times 10^6$ | |
| A5-2.5 | DP | $2.5 \times 10^6$ | |
| A5-5 | 200 µg/mouse | $5 \times 10^6$ | |

Preparation of Cell Suspensions

TABLE 9

Results of cell counting and preparation of cell suspensions ($10 \times 10^6$/ml)

| Grp | vol. (ml) | Dilutn. factor | Viable cells | Dead cells | % Viable cells | % Dead cells | Average viable cells | Total viable cells ($\times 10^6$) | EM-1 to add (ml) for suspension of $10 \times 10^6$ cells/ml |
|---|---|---|---|---|---|---|---|---|---|
| A1 | 10 | 16 | 115 | — | 100 | — | 112 | 179.2 | 17.9 |
|    |    |    | 109 | — | 100 | — |     |       |      |
| A2 | 10 | 16 | 50  | 4  | 92.6 | 7.4 | 47.5 | 76  | 7.6  |
|    |    |    | 45  | 2  | 95.7 | 4.3 |      |     |      |
| A3 | 10 | 16 | 80  | 4  | 95.2 | 4.8 | 80.5 | 128.8 | 12.8 |
|    |    |    | 81  | 5  | 94.2 | 5.8 |      |       |      |
| A4 | 10 | 16 | 87  | —  | 100  | —   | 89   | 142   | 14.2 |
|    |    |    | 91  | —  | 100  | —   |      |       |      |
| A5 | 10 | 16 | 120 | 2  | 98.4 | 1.6 | 112.5 | 180  | 18   |
|    |    |    | 105 | 2  | 98.1 | 1.9 |       |      |      |

Immunization

The immunization was performed by injecting 100 microliters of the emulsion (50 microliters into each hind footpad).

Treatment

Following the immunization step the mice were treated by s.c. injection of 200 µl from the designated Compound 1 DP or 12% captisol® treatment solutions, at the back of their neck.

In-Vitro Culture

Mice were sacrificed by cervical dislocation. LN were extracted from the hind legs and were transferred to a sterile petri dish containing about 5 mL RPMI. The cells were extracted by gentle squeezing of the tissue against a 200 micrometer mesh stainless steel net. The cells were collected and centrifuged at 300 G for 10 minutes at RT.

Single cell suspensions were prepared from pooled LN of each experimental group.

2.5 and 5.0 million cells/ml/well suspensions were cultured with Compound 1 RS (0-100 µg/ml) in EM-1.

Secretion of IFN-γ and TGF-β, as indication of cellular response, were determined by ELISA of culture media (48 hrs for IFN-γ and 72 hrs for TGF-β).

Preparations of Cell Suspensions ($5 \times 10^6$/ml)

The $10 \times 10^6$ cells/ml suspensions were diluted 1:2 by adding 5 ml EM-1 to 5 ml cells suspension.

Incubation of LN Cells Cultures in 48 Wells Plates 3 tissue culture plates were prepared. The following was added to each plate.

Background Control (Cells Incubated with Culture Media)
0.5 ml of cells suspension
0.5 ml of culture media (EM-1)

System of Positive Control (Cells Stimulated with Con A)
0.5 ml of cells suspension
0.5 ml of Con A 5 µg/ml in EM-1 (final conc. 2.5 µg/well)

Cells Incubated with Compound 1 Activation Solutions (Samples)
0.5 ml of cells suspension
0.5 ml of Compound 1 RS 6.25-200 g/ml (final conc. 3.125-100 µg/ml/well)

Incubation of LN Cells Cultures in 96 Wells Plates

After the 48-wells plates were prepared, 96-wells plates were prepared by applying 100 µl from the cell suspension and 100 µl from the activation solutions.

The culture plates were incubated at 37° C. in a humidified 5% $CO_2$ incubator, for either 48 or 72 hrs.

Supernatants Collection

The cultured plates were centrifuged at 300 g for 10 minutes at RT. Supernatants (850 μl from each well) were transferred either to mirror plates or to tubes. The supernatant was then divided into working aliquots (two aliquots of 200 and one aliquot of 450 μl), in order to avoid repeated freeze/thawing of the samples. Each tube was labeled with the following details:

1. Experimental code and time post incubation.
2. Group and sample number
3. Activator and concentration.
4. Date of sup collection The supernatants were stored at −20° C. until used for ELISA.

Results

TABLE 10

Summary of Groups
Experimental Groups:

| Immunization | | Treatment | | |
| --- | --- | --- | --- | --- |
| Exp. Groups | Immunization dose | Sub group | Article | In-vitro activation |
| A | 50 μg/mouse | A1 | 12% Captisol ® Placebo control | Compound 1 RS 3.125-100 μg/ml |
| | | A2 | Compound 1 25 μg/M | |
| | | A3 | Compound 1 50 μg/M | |
| | | A4 | Compound 1 100 μg/M | |
| | | A5 | Compound 1 200 μg/M | |

TABLE 11-A

Final cytokine concentrations
Final cytokine (pg/ml) (2.5 million cells/well)

| Compound 1 concentration | Placebo | 50 μg/M | 100 μg/M | 200 μg/M |
| --- | --- | --- | --- | --- |
| 3.125 μg/ml | 321.3 | 54.1 | 64.5 | 103.9 |
| 6.25 μg/ml | 238.6 | 81.8 | 116.1 | 126.1 |
| 12.5 μg/ml | 397.1 | 123.1 | 180.9 | 129.0 |
| 25 μ/ml | 655.5 | 215.1 | 262.8 | 240.3 |
| 50 μg/ml | 573.9 | 292.5 | 518.3 | 378.1 |
| 100 μg/ml | 926.0 | 531.8 | 582.7 | 524.1 |
| Con A | 322.6 | 356.2 | 337.4 | BQL |

TABLE 11-B

Final cytokin concentrations
Final cytokine (pg/ml) (5 million cells/well)

| Compound 1 concentration | Placebo | 25 μg/M | 50 μg/M | 100 μg/M | 200 μg/M |
| --- | --- | --- | --- | --- | --- |
| 3.125 μg/ml | 522.3 | BQL | 76.2 | 90.8 | 204.4 |
| 6.25 μg/ml | 634.8 | BQL | 109.2 | 157.8 | 244.1 |
| 12.5 μg/ml | 962.8 | 41.9 | 179.5 | 257.1 | 466.1 |
| 25 μ/ml | 967.4 | 70.0 | 277.9 | 421.7 | 660.5 |
| 50 μg/ml | 1338.8 | 104.2 | 373.4 | 739.7 | 922.5 |
| 100 μg/ml | 2010.2 | 185.2 | 547.0 | 995.5 | 1006.2 |
| Con A | 6839.8 | 2995.3 | 4837.0 | 10126.8 | 7722.8 |

The results are also presented in FIGS. 3-4.

Observations

IFN-γ Secretion

1. In the placebo group, a linear dose response upon Compound 1 activation in-vitro was shown. This graph resembles the graph obtained for the Ex-vivo model with the same immunization dose (50 μg/mouse) and culturing medium (EM-1).
2. There was a dose response upon Compound 1 activation in vitro within all the tested groups.
3. Significant inhibition of IFN-γ secretion was seen with all the doses used for treatment (an average of 95% inhibition with treated dose of 25 μg/mouse). A reverse correlation between the dose served for treatment and % inhibition can be found, mainly when $5 \times 10^6$ cells/well were used. When $2.5 \times 10^6$ cells/well were used, treatment of animals with 50 μg/mouse gave better inhibition than 100 or 200 μg. The point of 25 μg is missing (lack of cells).
4. A better inhibition was seen when $5 \times 10^6$ cells/well were used instead of $2.5 \times 10^6$ cells/well.
5. In the linear range of the graphs, SD of % inhibition was low.
6. A technical problem with Con A is apparent when $2.5 \times 10^6$ cells/well were used.

TGF-β Secretion

1. In the placebo group, no dose response upon in vitro activation with compound 1 was seen. TGF-β secreted level was below the detection limit of the ELISA in all other treatment groups.

EXAMPLE 6

Optimizations of Freeze Drying Cycle with Compound 1 and Captisol® for Injection (0, 0.5, 1.0 and 2.5 mg/Vial)

Purpose

The purpose of this study was to optimize the freeze drying cycle for Compound 1 with captisol® for injection to improve the shape of the lyophilization cake and avoid collapse and cracking. Thus it was decided to improve and optimize the lyophilization cycle. This cycle is transferred to the production lyophilizers for the manufacturing of the phase I batches.

Process Optimization

Batches of peptide at concentrations of 0.5 mg/ml 11.0 mg/ml, 2.5 mg/ml and Placebo were prepared and several freeze drying cycles were performed. The freeze drier used was an Edwards lyophilizer Lyoflex 0.6.

Solubility, water content and cake appearance were tested.

According to the obtained results a new lyophilization cycle for Compound 1 was selected. Due to the high percentage of solids (12%) and hence the condensed cake, the new process is longer than the lyophilization cycle in Example 3 and exhibits an additional primary drying stage. Table 12 summarizes the differences between the processes.

TABLE 12

| Step | Lyoph. cycle for Compound 1 and Captisol ® of Example 3 | New Lyoph. cycle for Compound 1 and Captisol ® |
|---|---|---|
| Loading | 5° C. | 5° C. |
| Freezing | 2 hours to −40° C. | 6 hours to −45° C. |
| Hold at low temp. | 3 hours to −40° C. | 3 hours to −45° C. |
| Primary Drying: | to 20° C. | to −20° C. |
| Stage I | 13 hours pressure 110 μbar | 19 hours pressure 150 μbar |
| Stage II | — | to 25° C. 13 hours pressure 150 μbar |
| Hold at 20° C. (25° C.) | 13 hours pressure 110 μbar | 8 hours pressure 150 μbar |
| Secondary drying: | | |
| Hold at 20° C. | 5 hours pressure 10 μbar | — |
| Storage at | 5° C. | 5° C. |
| Process time | 36 hours | 49 hours | neously once a week for 10 weeks either with Captisol® alone (n=8) or with 25 or 50 μg/mouse Compound 1 in Captisol® (n=9 and 10, respectively). These doses were selected since prior studies indicated that doses in this range were more effective in ameliorating SLE symptoms than the higher doses tested (100 and 200 μg/mouse). The same batch of drug substance was used in this study and in the first Phase I clinical trial with Compound 1.

The mice were followed for anti-dsDNA antibodies and for proteinuria. When the mice were sacrificed, the intensity of ICD was determined in kidneys.

As can be seen in FIG. 5, no significant differences between groups could be observed in the levels of dsDNA-specific antibodies after 10 treatment injections.

Table 13 also shows that the beneficial effect of treatment with Compound 1 could be observed starting from the $5^{th}$ injection and it was sustained up to the $10^{th}$ injection. The mean levels of proteinuria in the Captisol® control group were consistently higher than in the Compound 1-treated groups. Table 13 also shows that a reduction in the intensity of ICD was observed in kidneys of both Compound 1 dose groups. There was an overall trend showing that the lower dose (25 μg/mouse) was more effective than the higher dose (50 μg/mouse) in reducing the clinical symptoms of SLE in these mice.

TABLE 13

Clinical Symptoms of SLE in (NZBxNZW)F1 Mice Treated with 25 or 50 μg/mouse Compound 1 (in Captisol ®)

| Study Group | Mean Proteinuria ± SEM (g/L) Number of Weeks Following Treatment Initiation | | | | ICD[a] |
|---|---|---|---|---|---|
| | 5 | 7 | 8 | 10 | (Mean ± SEM) |
| Captisol ® | 1.81 ± 1.22 (n = 8) | 5.74 ± 3.13 (n = 8) | 4.5 ± 2.92 (n = 7)[b] | 4.46 ± 2.93 (n = 7)[b] | 2.29 ± 0.28 (n = 7) |
| Compound 1 (50 μg/mouse) | 0.75 ± 0.3 (n = 10) | 0.81 ± 0.3 (n = 10) | 1.09 ± 0.4 (n = 10) | 1.29 ± 0.3 (n = 10) | 1.90 ± 0.23 (n = 10) |
| Compound 1 (25 μg/mouse) | 0.16 ± 0.05 (n = 9) | 1.26 ± 1.09 (n = 9) | 0.5 ± 0.31 (n = 9) | 0.56 ± 0.3 (n = 9) | 1.22[c] ± 0.32 (n = 9) |

[a]ICD = Immune Complex Deposits. ICD intensity scale: 0 = none; 1 = moderate; 2 = severe; 3 = severe/extremely intense.
[b]The death of one animal with a high level of proteinuria resulted in a lower group mean.
[c]$p < 0.05$ (compared to Captisol ®-treated control mice; Mann-Whitney).

EXAMPLE 7

Effect of Compound 1 (Administered in Captisol®) on Lupus Symptoms in the SLE-Prone (NZBxNZW)F1 Female Mouse Patients participating in clinical trials are to be treated with Compound 1 using Captisol® (sulfobutyl ether beta-cyclodextrin sodium) as the excipient. For this reason, it was important to determine whether treatment of (NZBxNZW) F1 mice with the formulation of Compound 1 given in Captisol® would have the same beneficial effects on lupus symptoms as observed when this strain of mice was treated with Compound 1 in PBS.

To this end, (NZBxNZW)F1 female mice (about 8 months old) were divided into 3 groups that were treated subcuta- FIG. 6 shows representative sections of one kidney from each treatment group. The top row sections are from a Captisol®-treated mouse, the mid-row sections are from a mouse treated with 50 μg/mouse Compound 1 and the bottom row sections are from a mouse treated with 25 μg/mouse Compound 1. It can be seen that the intensity of immune complex deposits observed in kidney sections of mice treated with Compound 1 (dissolved in Captisol®) at either dose level was much lower than that observed in the control group.

EXAMPLE 8

Phase I Clinical Study

A Phase I, Multicenter, Randomised, Double-Blind, Placebo Controlled, Single Dose, Four-Arm Study to Assess the Tolerability and Safety of Compound 1 in Captisol® Subcutaneous Injection in SLE Subjects.

This was the first clinical study with Compound 1 in captisol® in humans, conducted in France. Its main objective was to evaluate tolerability and safety of Compound 1 in captisol®, administered as a single sc injection to SLE subjects. Its secondary objective was to evaluate immunological responses following a single sc dose of Compound 1 in captisol® in these subjects.

Thirty-six (36) subjects participated in the study. To be eligible for inclusion in the study, SLE patients must have fulfilled at least four criteria used for the diagnosis of lupus by the American College of Rheumatology. Patients must also have had stable, mild/moderate disease and score less than or equal to 10 on the SLE Disease Activity Index, SLEDAI.

Each patient received a single sc injection of reconstituted Compound 1 for injection or its matching placebo (Captisol®) according to the following group assignment:
Group A: Placebo (Captisol®)
Group B: 0.5 mg Compound 1 in Captisol®
Group C: 1 mg Compound 1 in Captisol®
Group D: 2.5 mg Compound 1 in Captisol®

A standard battery of safety tests, including blood and urine collection for laboratory tests, was performed at screening, during the day of dosing, at 24 hours post-dose and at 2, 4 and 8 weeks following dosing. Prior to dosing, and on scheduled follow-up visits, blood samples were withdrawn for SLE-related immunological tests, anti-Compound 1 antibodies and PBL proliferation assay. The following immunology tests were performed:
Coomb's (direct and indirect)
C3, C4 and CH50
Total IgG, IgM and IgA
ANA, anti-dsDNA (Farr assay), anti-ssDNA
Anti-ENA (including anti-La, anti-Ro, anti-RNP, anti-Sm)
Anti-cardiolipin antibodies
VDRL
FTA antibodies
Rheumatoid factor The safety and tolerability of Compound 1 in captisol® in the subject population was evaluated on the basis of the following criteria:
Occurrence of AEs, including SLE flare
Vital signs
12-lead ECG
Changes in physical examination
Routine clinical laboratory tests
SLEDAI score
Immunological test results Phase Ia Clinical Study Details Study Principal Investigators and Respective Study Sites: Six (6) study centers in France:Prof. Jean Charles Piette (Hopital La Pitie Salpetriere, Paris), Prof Oliver Meyer (Hopital Bichat, Paris), Prof. Jean Revuz (Hopital Henri Mondor, Creteil), Prof. Loic Guillevin (Hopital Avicenne, Bobigny), Prof. Eric Hachulla (Hopital Claude Huriez, Lille Cedex), Prof. Xavier Mariette (Hopital Bicetre, Kremlin Bicetre).

Compound 1 (in Captisol®), Placebo, Water for Injection-Ampoules, Dose and Mode of Administration:

Vials of Compound 1 in Captisol® (120 mg/vial) were injected subcutaneously as a single dose per subject in the following dosages: 0.5 mg Compound 1/vial in Captisol®, 1 mg Compound 1/vial in Captisol® and 2.5 mg Compound 1/vial in Captisol®. Placebo for Compound 1: 120 mg Captisol®/vial (identical in appearance to vials of Compound 1 in Captisol®).

Methodology

This was a multi-center, randomized; double blind, placebo-controlled, four-arm study, using a single subcutaneous injection of Compound 1 or placebo. SLE patients were screened up to 21 days prior to baseline procedures. Each eligible subject was randomized to one of the 4 treatment groups: subcutaneous injection of either 0.5, 1 or 2.5 mg Compound 1 or its matching placebo. All subjects were admitted to the clinic on pre-dosing day. Each subject received a single dose of one of the above listed treatments. Subjects were discharged from the clinic 24 hours after dosing. Subjects were further monitored at weeks 2, 4 and 8 following dosing. Blood samples (serum and whole blood) for safety laboratory tests were withdrawn at Screening, Dosing Day (pre-dose), Day 2 (post dose), at Weeks 2, 4 and 8 (Termination visit). Blood samples for immunological tests were withdrawn at: Screening, Dosing Day (pre-dose) and at Weeks 4 and 8. Peripheral blood lymphocytes (PBL) proliferation was evaluated at Dosing Day (pre-dose) and at Weeks 2, 4 and 8.

Number of Subjects (Total and for Each Treatment):

Thirty six (36) subjects were randomized into this study as follows; 9 subjects into the 0.5 mg treatment group, 9 subjects into 1 mg treatment group, 10 subjects into the 2.5 mg treatment group, and 8 subjects into the placebo treatment group.

Diagnosis and Main Criteria for Inclusion:

Eligible subjects for this study were SLE patients who fulfilled at least four diagnostic criteria of the American College of Rheumatology (ACR). Their disease condition had to be stable, mild to moderate with a score equal to or less than 10 on the SLE disease activity index, year 2000 updated (SLEDAI 2K).

Excluded from participation were SLE patients who reported unstable or severe asthma, stroke, acute myocardial infarction, unstable angina, cerebral hemorrhage and pulmonary embolism during the six months prior to study screening. SLE patients who had any clinically significant or unstable medical or surgical conditions, diabetes mellitus, liver disease (cirrhosis, active hepatitis, portal hypertension, and/or ascites), clinically significant hypertension, a medical history of any malignancy, dialysis, or chronic obstructive pulmonary disease (COPD) were also excluded from study participation.

Also excluded from study participation were SLE patients who underwent plasmapheresis or were treated during the three months prior to screening with one of the drugs listed below: prednisone 30 mg/day or greater (or an equivalent dose of another corticosteroid), intravenous corticosteroids, intravenous immunoglobulin G (IgG), oral anticoagulants and any cytotoxic agents (e.g. azathioprine, chlorambucil, cyclophosphamide, mycophenolate mofetil, methothrexate, tacrolimus.

In addition, SLE patients initiating treatment with corticosteroids (more than +10 mg/day prednisone, or an equivalent dose of another corticosteroid) and/or anti-malarials, during the last 3 months prior to screening were excluded from the study.

While an effort was made to retain baseline SLE medical treatments throughout the course of the study, investigators could nevertheless change participant medical treatment at any time during the study to maintain and optimize patient welfare.

Criteria for Evaluation

Safety:

The following safety parameters were assessed at Screening, during the hospitalization and at follow-up visits including Termination visit: vital signs (systolic blood pressure, diastolic blood pressure, pulse, oxygen saturation, temperature and weight), 12-lead ECG, change in physical examination and clinical routine laboratory safety tests. Adverse events were recorded at the Dosing Day and at each visit thereafter.

Immunology:

SLE-related immunological tests were performed at Screening, during the hospitalization and at follow-up visits including Termination visit.

Drug-related immunological responses were followed by using the PBL proliferation assay and anti-Compound 1 antibodies assay at the Dosing Day and at follow-up visits including Termination visit.

Disease Activity:

Disease activity assessment using the SLE disease activity index score, year 2000 updated (SLEDAI 2K) was assessed at Screening, during the hospitalization and at follow-up visits including Termination visit.

Statistical Methods:

SAS® version 9.0 software was used to analyze and present data collected during this study. No power calculation was performed and no formal hypothesis testing was conducted for this Phase Ia study.

Adverse Experiences

The incidence and the frequency of adverse experiences was presented by System Organ Class and preferred terminology according to MedDRA dictionary version 5.0. The data is tabulated by treatment group.

Clinical Laboratory Data

Descriptive statistics of laboratory values including number of observations, mean, standard deviation, minimum and maximum were determined for Screening, Day 1 (pre dose), Day 2, Week 2, 4 and 8 are presented by treatment group. Changes from baseline to each time point/visit are also presented for each visit by treatment assignment. Percent of abnormal results (low and high, where applicable) are presented on a parameter basis, by treatment group and visit/time point. Shift analyses from baseline to 24-hours post dose and from baseline to termination visit were performed.

Vital Signs

Descriptive statistics for vital signs including number of observations, mean, standard deviation, median, minimum and maximum values were determined for Screening, Day 1 (pre and post dose, and at each time point) Day 2, Weeks 2, 4 and 8 are tabulated by the assigned treatment. Changes from baseline to each time point/visit is presented in by visit and treatment assignment.

Weight

Descriptive Statistics of Weight (kg) at baseline, termination and change from baseline is presented by treatment group.

ECG

Descriptive statistics of ECG parameters at baseline, termination and changes from baseline are presented. Shift analysis is presented as tables of shift from baseline to termination between normal/abnormal or present/absent ECG parameters. Potentially clinically significant (PCS) QTc (Bazett) measurements were identified according to the predefined criteria. Tables of shift analysis between PCS and non-PCS Absolute QTc (Bazett) and incidence table of PCS change in QTc (Bazett) from baseline to any visit are presented.

Physical Examination

Physical examination results are analyzed by incidence of subjects with abnormal or normal findings for each body system at Baseline and Termination visit. Shift analysis between normal to abnormal and vice versa was also applied. When no change from baseline occurred, it was defined as "other".

Compound 1 Related Immunological Tests

For immunological parameters, descriptive statistics, including number of observations, mean, standard deviation, median, minimum and maximum values were calculated and are presented by treatment group and visit. Change from baseline to each follow-up visit is also presented by treatment group. Where applicable, number and percent of subjects with negative/positive results is presented by treatment group and visit.

SLEDAI 2K

Descriptive statistics, including mean, standard deviation, median, minimum and maximum values of SLEDAI 2K are presented.

Results of Phase Ia Clinical Study:

Subject Disposition and SLE Characteristics

Thirty six (36) study subjects entered and completed this study per protocol. The majority of subjects (34) in all treatment groups were female (94.4%) and Caucasian (30, 83.3%). The mean age for all treatment groups was 35.6 years (range of means from 32 to 39 years). Most of the subjects (91.7%) had between 4 to 6 American College of Rheumatology (ACR) diagnostic criteria and a mean group SLEDAI 2K score ranged from 2.1 to 4.1.

Safety Results

There was no prominent difference between study drug treatment groups and the placebo group in the incidence of AEs. The most common AEs in all groups were headache, classified as mild or moderate in nature and injection site reaction classified as mild in nature. Dose response was not seen. No serious adverse event (SAE) or AE classified as severe occurred during the study.

No clinically significant effect attributable to study drug was seen for hematology, biochemistry or urinalysis values.

No clinically significant effect attributable to the study drug was seen for vital signs parameters (systolic blood pressure, diastolic blood pressure, pulse, oxygen saturation).

No clinically significant effect attributable to the study drug was seen for temperature and weight.

No differences of clinical significance were seen between Compound 1-treated groups and placebo for categorical ECG measurements and digitized ECG parameters. No PCS QTc absolute value and no QTc change from baseline >60 msec was recorded. A similar number of subjects in Compound 1-treated and placebo groups had QTcB change from baseline between 30 and 60 msec.

No clinically significant effects of Compound 1 on physical exam were noted.

Immunology Results

Evaluation of serum samples from all subjects indicated that a single subcutaneous administration of Compound 1 at the dose levels of 0.5, 1 and 2.5 mg/patient did not induce the development of anti-Compound 1 specific antibodies. Seven subjects had a response to Compound 1 above the cut-off. These elevated levels of antibodies were already present prior to dosing. No increase in the levels of antibodies was observed in the follow up period (two months) of the study. The sera of these subjects were analyzed for the isotype of the reactive antibodies. The response in two of the subjects was associated with the IgM isotype and with the IgG isotype in two others. None of the seven had specific IgE antibodies.

The peripheral blood lymphocytes (PBL) assay showed that 50% of the subjects (18) were classified as responders (SI>2) with similar distribution in all treatment groups. The T cell response was relatively low and no association between Compound 1 treatment dose or concentration used in the assay and responder/non-responder status could be detected, taking into consideration that only a single SC dose of the study drug was administered. Also, no indication of increased incidence of responder status over time was observed. The tetanus toxoid (TTX) assay that serves as a safety control shows that the response to TTX was preserved throughout the study period in all treatment groups indicating that Compound 1 in captisol® did not change the immunological response to TTX recall antigen.

The immunological findings are the result of the administration of only a single dose of the study drug Compound 1.

Disease Activity Results

No clinically significant effects of Compound 1 on the SLEDAI score (change of ≧3, ≦12 points) were noted during the study except for one subject in the 0.5 mg treatment group for whom a change in the SLEDAI score of 2 to 10 points was recorded between baseline and week 4 on the basis of an urinalysis showing pyuria. This urinalysis finding was not confirmed by the investigator as a lupus flare per protocol definition and was resolved with no treatment change.

Conclusions

This Phase Ia study showed that a single subcutaneous injected dose of Compound 1 of 0.5, 1 or 2.5 mg in 120 mg Captisol® was safe and well tolerated and allows continuation to a phase Ib multiple dose study.

EXAMPLE 9

Phase Ib Clinical Study

A Phase I, Multicenter, Bi-National, Randomized, Double-Blind, Four-Arm, Placebo Controlled, Multiple Dose Study to Assess the Tolerability and Safety of Compound 1 in Captisol® Subcutaneous Injections in SLE Subjects This study is being performed in order to evaluate the safety and tolerability of repeated Compound 1 sc administration to SLE subjects. The study's secondary objective is to evaluate immunological responses following repeated sc administration of Compound 1 in Captisol® in SLE subjects.

Compound 1 is given in doses of 0.5, 1.0 or 2.5 mg in Captisol®. The investigational product is administered every other day (excluding weekends) for a total of 12 sc injections, i.e. 3 doses a week for 4 weeks. Subjects are monitored on planned visits scheduled at 2, 4, 8 and 12 weeks after start of dosing. Safety and tolerability are evaluated using tests similar to those described in the Phase Ia Clinical Study above.

Results

This Phase Ib study shows that multiple subcutaneous injected doses of Compound 1 of 0.5, 1 or 2.5 mg in 120 mg Captisol® are safe and well tolerated.

What is claimed is:

1. A pharmaceutical composition comprising
   an aqueous carrier;
   from 0.1 mg/ml to 2.5mg/ml of the composition of an acetate salt of a peptide having the structural formula NH$_2$-Gly Tyr Tyr Trp Ser Trp Ile Arg Gln Pro Pro
      Gly Lys Gly Glu Glu Trp Ile Gly-COOH (SEQ ID NO:1); and from 70 mg/ml to 170 mg/ml of the composition of hepta-(sulfobutyl ether)-β-cyclodextrin or a salt of hepta-(sulfobutyl ether)-β-cyclodextrin,
   wherein the peptide and the hepta-(sulfobutyl ether)-β-cyclodextrin or a salt of hepta-(sulfobutyl ether)-β-cyclodextrin are dissolved in the aqueous carrier; and wherein the pharmaceutical composition has a pH between 6.5 and 8.5.

2. The pharmaceutical composition of claim 1, wherein the concentration of the acetate salt of the peptide is at least 0.5 mg/ml.

3. The pharmaceutical composition of claim 2, wherein the concentration of the acetate salt of the peptide is from 0.5 to 2.5 mg/ml.

4. The pharmaceutical composition of claim 2, wherein the concentration of the salt of hepta-(sulfobutyl ether)-β-cyclodextrin is 120 mg/ml, and wherein the pH of the pharmaceutical composition is between 7.5 and 8.5.

5. The pharmaceutical composition of claim 4, wherein the concentration of the acetate salt of the peptide is 1.0 mg/ml.

6. The pharmaceuticalcomposition of claim 4, wherein the concentration ofthe acetate salt of the peptide is 2.5 mg/ml.

7. A method of alleviating symptoms of systemic lupus erythematosus (SLE) in a human subject comprising administering to the human subject the pharmaceutical composition of claim 1 an amount effective to alleviate the symptoms of SLE in the human subject.

8. A process for manufacturing the pharmaceutical composition comprising the steps of:
   a) preparing a solution of a hepta-(sulfobutyl ether)-β-cylodextrin or a salt of hepta-(sulfobutyl ether)-β-cyclodextrin in an aqueous carrier at a predetermined concentration;
   b) adding a predetermined amount of a pharmaceutically acceptable salt of the peptide NH$_2$-Gly Tyr Tyr Trp Ser Trp Ile Arg Gln Pro Pro Gly Lys Gly Glu Glu Trp Ile Gly-COOH (SEQ ID NO:1) to the solution of step a);
   c) adjusting the pH of the solution of step b) until the peptide dissolves in the solution; and
   d) if necessary, adjusting the pH of the solution of step c) to a pH of 4-9, thereby manufacturing the pharmaceutical composition.

9. A pharmaceutical composition prepared by the process of claim 8.

10. A process of lyophilizing the pharmaceutical composition of claim 1, comprising the steps of:
    a) lowering the temperature of the pharmaceutical composition to -40° C.;
    b) holding the temperature at -40° C. for a predetermined time;
    c) raising the temperature of the solution to 20° C.;
    d) holding the temperature at 20° C. for a predetermined time; and
    e) reducing the pressure in step d) to a pressure suitable for lyophilization and holding the temperature at 20° C. for a predetermined time, thereby lyophilizing the pharmaceutical composition.

11. The process of claim 10, wherein
    step a) is performed within 2 hours;
    step b) is performed within 3 hours;
    step c) is performed over 13 hours and at a pressure of 110 µbar;
    step d) is performed over 13 hours and at a pressure of 110 µbar; and
    step e) is performed over 5 hours and the pressure is reduced to 10 µbar.

12. A lyophilized pharmaceutical composition prepared by the process of claim 10.

13. A process of lyophilizing the pharmaceutical composition of claim 1, comprising the steps of:
    a) lowering the temperature of the pharmaceutical composition to -45° C.;
    b) holding the temperature at -45° C. for a predetermined time;
    c) raising the temperature of the solution to -20° C.;
    d) raising the temperature of the solution to 25° C.; and
    e) holding the temperature at 25° C. for a predetermined time, thereby lyophilizing the pharmaceutical composition.

14. The process of claim 13, wherein
    step a) is performed within 6 hours;
    step b) is performed within 3 hours;
    step c) is performed over 19 hours and at a pressure of 150 µbar;
    step d) is performed over 13 hours and at a pressure of 150 µbar; and
    step e) is performed over 8 hours and at a pressure of 150 µbar.

15. A lyophilized pharmaceutical composition prepared by the process of claim 13.

16. A lyophilized pharmaceutical composition comprising a pharmaceutically acceptable salt of a peptide having the structural formula NH$_2$-Gly Tyr Tyr Trp Ser Trp Ile Arg Gln Pro Pro
Gly Lys Gly Glu Glu Trp Ile Gly-COON (SEQ ID NO:1); and a hepta- (sulfobutyl ether) -β-cyclodextrin or a salt thereof.

17. A packaged pharmaceutical composition comprised of:
    a packaging material; and
    the lyophilized pharmaceutical composition of claim 16.

18. The lyophilized pharmaceutical composition of claim 15, wherein the water content of the pharmaceutical composition is less than 5%.

19. The lyophilized pharmaceutical composition of claim 18, wherein the water content of the pharmaceutical composition is less than 4.0%.

20. The lyophilized pharmaceutical composition of claim 19, wherein the water content of the pharmaceutical composition is less then 3.5%.

21. The pharmaceutical composition of claim 1, wherein the pharmaceutical composition is iso-osmotic.

22. The pharmaceutical composition of claim 1 formulated for subcutaneous administration.

23. The pharmaceutical composition of claim 1 further comprising HC1 or NaOH.

24. The pharmaceutical composition of claim 1 wherein the salt of hepta-(sulfobutyl ether)-β-cyclodextrin is a sodium salt.

25. The pharmaceutical composition of claim 4, wherein the concentration of the acetate salt of the peptide is 0.5 mg/ml.

* * * * *

SEQUENCE LISTING

```
<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: A synthetic peptide of 19 amino acids based on
      the complementarity-determining region 1 (CDR1) of the
      human anti-dsDNA mAb denoted 16/6 Id

<400> SEQUENCE: 1

Gly Tyr Tyr Trp Ser Trp Ile Arg Gln Pro Pro Gly Lys Gly Glu Glu
1               5                   10                  15

Trp Ile Gly
```